US009750823B2

(12) United States Patent
Fisher et al.

(10) Patent No.: US 9,750,823 B2
(45) Date of Patent: Sep. 5, 2017

(54) USE OF A TRUNCATED CCN1 PROMOTER FOR CANCER DIAGNOSTICS, THERAPEUTICS AND THERANOSTICS

(71) Applicant: Virginia Commonwealth University, Richmond, VA (US)

(72) Inventors: Paul B. Fisher, Richmond, VA (US); Swadesh K. Das, Richmond, VA (US); Rupesh Dash, Richmond, VA (US); Devanand Sarkar, Richmond, VA (US); Siddik Sarkar, Richmond, VA (US); Jolene Windle, Richmond, VA (US)

( * ) Notice: Subject to any disclaimer, the term of this patent is extended or adjusted under 35 U.S.C. 154(b) by 0 days.

(21) Appl. No.: 14/895,247

(22) PCT Filed: Jun. 4, 2014

(86) PCT No.: PCT/US2014/040796
§ 371 (c)(1),
(2) Date: Dec. 2, 2015

(87) PCT Pub. No.: WO2014/209553
PCT Pub. Date: Dec. 31, 2014

(65) Prior Publication Data
US 2016/0101193 A1    Apr. 14, 2016

Related U.S. Application Data

(60) Provisional application No. 61/830,837, filed on Jun. 4, 2013.

(51) Int. Cl.
| | |
|---|---|
| *A61K 48/00* | (2006.01) |
| *A61K 47/00* | (2006.01) |
| *A61K 49/00* | (2006.01) |
| *C12N 15/00* | (2006.01) |
| *C12N 5/00* | (2006.01) |
| *A01K 67/027* | (2006.01) |
| *A61K 35/761* | (2015.01) |
| *C12N 15/86* | (2006.01) |
| *C12N 15/85* | (2006.01) |

(52) U.S. Cl.
CPC ...... *A61K 48/0058* (2013.01); *A01K 67/0275* (2013.01); *A61K 35/761* (2013.01); *A61K 49/005* (2013.01); *A61K 49/0008* (2013.01); *C12N 15/86* (2013.01); *A01K 2207/12* (2013.01); *A01K 2217/052* (2013.01); *A01K 2217/206* (2013.01); *A01K 2227/105* (2013.01); *A01K 2267/0331* (2013.01); *A01K 2267/0393* (2013.01); *C12N 2015/8536* (2013.01); *C12N 2015/8572* (2013.01); *C12N 2710/10332* (2013.01); *C12N 2830/008* (2013.01); *C12N 2830/34* (2013.01)

(58) Field of Classification Search
None
See application file for complete search history.

(56) References Cited

U.S. PATENT DOCUMENTS

| | | |
|---|---|---|
| 4,405,712 A | 9/1983 | Vande Woude et al. |
| 4,650,764 A | 3/1987 | Temin et al. |
| 5,175,384 A | 12/1992 | Krimpenfort et al. |
| 5,191,151 A | 3/1993 | Eriksen et al. |
| 5,252,479 A | 10/1993 | Srivastava |
| 6,018,097 A | 1/2000 | Selden et al. |
| 6,080,912 A | 6/2000 | Bremel et al. |
| 6,262,335 B1 | 7/2001 | Hsiao et al. |
| 6,451,571 B1 | 9/2002 | Loeb et al. |
| 6,897,024 B2 | 5/2005 | Bussemakers et al. |
| 7,220,508 B2 | 5/2007 | Watakabe et al. |
| 7,247,297 B2 | 7/2007 | Weichselbaum et al. |
| 7,321,030 B2 | 1/2008 | Hamada |
| 7,364,727 B2 | 4/2008 | Li et al. |
| 7,816,131 B2 | 10/2010 | Hung et al. |
| 8,034,914 B2 | 10/2011 | Hochberg |
| 2002/0003791 A1 | 1/2002 | Hayata |
| 2006/0179501 A1 | 8/2006 | Chan et al. |
| 2007/0088142 A1 | 4/2007 | Ikeda et al. |
| 2008/0213220 A1 | 9/2008 | Fisher et al. |
| 2009/0311664 A1 | 12/2009 | Fong et al. |
| 2010/0330197 A1* | 12/2010 | Higashiguchi ........ A23L 33/175 424/638 |
| 2011/0136221 A1 | 6/2011 | Black |

(Continued)

FOREIGN PATENT DOCUMENTS

| | | |
|---|---|---|
| WO | WO-89/05345 | 6/1989 |
| WO | WO-90/06997 | 6/1990 |
| WO | WO-92/05266 | 4/1992 |

(Continued)

OTHER PUBLICATIONS

Sporn et al. (2000, Carcinogenesis 21: 525-530).*
Thoppil et al. (2011, World Journal of Hepatology 3: 228-249).*
Costello et al. (2012, Journal of Gastrointestinal Cancer 43: 570-578).*
Cao et al (2010, Clinical and Experimental Pharmacology and Physiology 37:108-114).*
Prestwich et al (2008, Clinical Medicine: Oncology. 2:83-96).*
Al-Madhoun et al., "Evaluation of Human Thymidine Kinase 1 Substrates as New Candidates for Boron Neutron Capture Therapy," Cancer Res. 64(17): 6280 (2004).
Berkner. "Development of adenovirus vectors for the expression of heterologous genes," Biotechniques 6: 616-626 (1988).
Blaese et al., "T Lymphocyte-Directed Gene Therapy for ADA-212 SCID: Initial Trial Results After 4 Years," Science 270: 475-479 (1995).
Cai et al., "The improved syntheses of 5-substituted 2'-[18F]fluoro-2'-deoxy-arabinofuranosyluracil derivatives ([18F]FAU, [18F]FEAU, [18F]FFAU, [18F]FCAU, [18F]FBAU and [18F]FIAU) using a multistep one-pot strategy," Nuclear Medicine and Biology 38(5): 659-666 (2011).

(Continued)

*Primary Examiner* — Christopher M Babic
*Assistant Examiner* — Kimberly A Aron
(74) *Attorney, Agent, or Firm* — Foley & Lardner LLP

(57) ABSTRACT

Recombinant vectors in which expression of one or more elements (e.g. genes required for viral replication, detectable imaging agents, therapeutic agents, etc.) is driven by a truncated CCN 1 cancer selective promoter (tCCN1-Prom) are provided, as are cells and transgenic animals that contain such vectors. The vectors are used in cancer therapy and/or diagnostics, and the transgenic mice are used to monitor cancer progression, e.g. in screening assays.

19 Claims, 11 Drawing Sheets

(56) References Cited

U.S. PATENT DOCUMENTS

2013/0263296 A1   10/2013   Pomper et al.

FOREIGN PATENT DOCUMENTS

| WO | WO-92/07573 | 5/1992 |
|---|---|---|
| WO | WO-92/14829 | 9/1992 |
| WO | WO-2010/062975 | 6/2010 |

OTHER PUBLICATIONS

Chan et al., "Evaluation of F-18-labeled 5-iodocytidine (18 F-FIAC) as a new potential positron emission tomography probe for herpes simplex virus type 1 thymidine kinase imaging," Nuclear Medicine and Biology 38(7): 987-995 (2011).
Cotten et al., "High-efficiency receptor-mediated delivery of small and large (48 kilobase gene constructs using the endosome-disruption activity of defective or chemically inactivated adenovirus particles," Proc. Natl. Acad. Sci. USA 89(13): 6094-6098 (1992).
Danos et al., "Safe and efficient generation of recombinant retroviruses with amphotropic and ecotropic host ranges," Proc. Natl. Acad. Sci. USA 85(17): 6460-6464 (1988).
Dash et al., "Apogossypol derivative BI-97CI (Sabutoclax) targeting Mcl-I sensitizes prostate cancer cells to mda-7/IL-24-mediated toxicity." Proc. Natl. Acad. Sci. USA 108: 8785-8790 (2011).
Dash et al., "Developing an effective gene therapy for prostate cancer: new technologies with potential to translate from the laboratory into the clinic," Discov Med 11: 46-56 (2011).
Donahue et al., "Reduction in SIV replication in rhesus macaques infused with autologous lymphocytes engineered with antiviral genes," Nature Medicine 4(2):181-186 (1998).
Doronin et al., "Tissue-Specific, Tumor-Selective, Replication-Competent Adenovirus Vector for Cancer Gene Therapy," J. Virol. 75(7): 3314-3324 (2001).
Freireich et al., "Quantitative comparison of toxicity of anticancer agents in mouse, rat, hamster, dog, monkey, and man," Cancer Chemother. Rep. 50(4): 219-44 (1966).
Geller et al., "A Defective HSV-1 Vector Expresses Eschirichia coli beta-galactosidase in Cultured Peripheral Neurons," Science 241: 1667-1669 (1988).
Gilad et al., "Artificial reporter gene providing MRI contrast based on proton exchange," Nature Biotechnology 25(2): 217-219 (2007).
Gilad et al., "MRI Reporter Genes," J. Nucl. Med. 49(12): 1905-1908 (2008).
Goldman et al., "Lentiviral Vectors for Gene Therapy of Cystic Fibrosis," Human Gene Therapy 10: 2261-2268 (1997).
Graham et al., "Manipulation of Adenovirus Vectors," Methods in Mol. Biol.: Gene Transfer and Expression Protocols 7: 109-127 (1991).
Greelish et al., "Stable restoration of the sarcoglycan complex in dystrophic muscle perfused with histamine and a recombinant adeno-associated viral vector," Nature Med. 5:439-443 (1999).
Hallenbeck et al., "A Novel Tumor-Specific Replication-Restricted Adenoviral Vector for Gene Therapy of Hepatocellular Carcinoma," Human Gene Therapy 10(10): 1721-1733 (1999).
Han et al., "Regulation of Cyr61/CCN1 gene expression through RhoA GTPase and p38MAPK signaling pathways," Eur J Biochem 270(16): 3408-21 (2003).
Herzog et al., "Long-term correction of canine hemophilia B by gene transfer of blood coagulation factor IX mediated by adeno-associated viral vector," Nature Medicine 5(1): 56-63 (1999).
Holloway et al., "Increased expression Cyr61 (CCN1) identified in peritoneal metastases from human pancreatic cancer," J Am Coll Surg 200(3): 371-377 (2005).
International Preliminary Report on Patentability for PCT/US2014/040796, issued Dec. 8, 2015.
International Search Report for PCT/US2014/047096, mailed Oct. 15, 2014.
Iordanova et al., "In vivo magnetic resonance imaging of ferritin-based reporter visualizes native neuroblast migration," Neuroimage 59(2):1004-1012 (2012).
Kafri et al., "Sustained expression of genes delivered directly into liver and muscle by lentiviral vectors," Nature Genetics 17(3): 314-317 (1997).
Kurihara et al., "Selectivity of a replication-competent adenovirus for human breast carcinoma cells expressing the MUC1 antigen," J. Clin. Invest. 106: 763-771 (2000).
Lee et al., "Selective Activation of Ceruloplasmin Promoter in Ovarian Tumors: Potential Use for Gene Therapy," Cancer Res. 64(5): 1788 (2004).
Li et al., "Assessment of Recombinant Adenoviral Vectors for Hepatic Gene Therapy," Human Gene Therapy 4:403-409 (1993).
Lv et al., "Cyr61 is up-regulated in prostate cancer and associated with the p53 gene status," J Cell Biochem 106(4): 738-44 (2009).
Meyuhas et al., "Key role for cyclic AMP-responsive element binding protein in hypoxia-mediated activation of the angiogenesis factor CCNI (CYR61) in tumor cells," Mol Cancer Res. 6(9): 1397-1409 (2008).
Mocarski et al "Viral Vectors." Gluzman and Hughes (eds.). Cold Spring Harbor Laboratory, Cold Spring Harbor, N.U., 1988, pp. 78-84.
Muller et al., "Synthesis and evaluation of a C-6 alkylated pyrimidine derivative for the in vivo imaging of HSV1-TK gene expression," Nuclear Medicine and Biology 39(2): 235-246 (2012, in press 2011).
O'Brien et al., "Expression of cyr61, a growth factor-inducible immediate-early gene," Mol Cell Biol 10(7): 3569-77 (1990).
O'Kelly et al., "Functional domains of CCN1 (Cyr61) regulate breast cancer progression," Int J Oncol 33(1): 59-67 (2008).
Onodera et al., "Development of Improved Adenosine Deaminase Retroviral Vectors," J. Virol. 72(3):1769-1774 (1998).
Piccini et al., "Vaccinia virus as an expression vector," Meth. Enzymology 153: 545-563 (1987).
Rodriguez et al., "Prostate Attenuated Replication Competent Adenovirus (ARCA) CN706: A Selective Cytotoxic for Prostate-specific Antigen-positive Prostate Cancer Cells," Cancer Res. 57(13): 2559-2563 (1997).
Sarkar et al., "Chemoprevention gene therapy (CGT): novel combinatorial approach for preventing and treating pancreatic cancer." Curr Mol Med 13(7): 1140-1149 (2012).
Shackleford et al., "Construction of a clonable, infectious, and tumorigenic mouse mammary tumor virus provirus and a derivative genetic vector," Proc. Natl. Acad. Sci. USA 85: 9655-9659 (1988).
Snyder et al., "Correction of hemophilia B in canine and murine models using recombinant adeno-associated viral vectors," Nature Medicine 5(1): 64-70 (1999).
Terada et al., "Cyr61 is regulated by cAMP-dependent protein kinase with serum levels correlating with prostate cancer aggressiveness," Prostate 72(9): 966-76 (2012).
Venkatesan et., "The potential of celecoxib-loaded hydroxyapatite-chitosan nanocomposite for the treatment of colon cancer," Biomaterials 32(15): 3794-3806 (2011).
Wang et al., "Sustained correction of bleeding disorder in hemophilia B mice by gene therapy," Proc. Natl. Acad. Sci. USA 96: 3906-3910 (1999).
Zabner et al., "Safety and efficacy of repetitive adenovirus-mediated transfer of CFTR cDNA to airway epithelia of primates and cotton rats," Nature Genetics 6:75-83 (1994).
Extended Search Report issued on European Appl. 14817622.5, mailed Oct. 12, 2016.

* cited by examiner

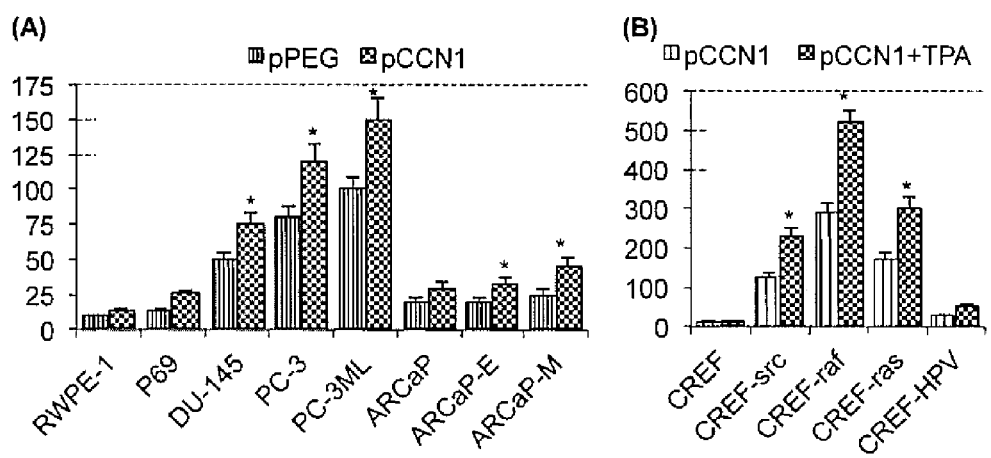
Figure 1A and B

TCCAAAAACAAACAAGTACAACATACCCAAAAGAGGGAAGGGCTGGAGGAG
TGGGGGAGACCTCTGCCTGGGAATTTGCCAGACGATGGGCAAGTTTCCCC
CCGCCCCACCCCCCCCCGCCTTTTCATTCATAAATGCCACTGTGGGTAT
TAATTTGCAATTCACTGAACTTTGCTAATAAACATCATGCCAAAGCTTTGGGA
CTTGTTCCGAACACGCCTCTTTGAAGTCCACAAATATTCCTGACTCAGAGAC
ACACTCCTCTTCCCCGTTCTACTCTTTCAACAGATAACTTGCCTCTCACCTTC
GCTGTAAAAAAGCAAACAGCTCACTGCCTTCCCGGGTGAGGGCTTCAGTGG
CTGCCCGGTCAACTCGCATCACCAAACAAAACGACTTTTGTTCCTCCCTCTC
AGGTCCTCCCACCCACCCAGTCCAGGCAAAGTTCTGAACTGGCCCCCTCGC
CCCTCACGACCCTCCAACTACCATCACCACCATCACGCCCCAAAGAACCCT
TCCCAACATAAGTCGTAATTTAAGGTGGAAAAAACGAACTGTTTTCTTGACG
GGTCTGGGACACACACACACACACACACACACACACCGAACTGTTTT
CTTGACGGGTCTGGGAGACACACACACACACACACACACACACACACAC
ACACACACACAAAGGTGCAATGGGGCCAGGGGAGGCGCTTGGCAGCAG
CCCGCGCCAACCAGCATTCCTGAGATGTTTGAGAATTCTGGAACGCGCAGA
CAGAGCCGACGTCACTGCAACACGCGGCGCCTCCGCCGGCCCGTATAAAA
GGCGGGCTCCGGGCGCC (SEQ ID NO: 1)

Figure 10

USE OF A TRUNCATED CCN1 PROMOTER FOR CANCER DIAGNOSTICS, THERAPEUTICS AND THERANOSTICS

CROSS-REFERENCE TO RELATED APPLICATIONS

This application is a U.S. national stage application under 35 U.S.C. §371 of International Application No. PCT/US2014/040796, filed Jun. 4, 2014, which claims the benefit of U.S. Provisional Application No. 61/830,837, filed Jun. 4, 2013, which are incorporated herein by reference in their entireties.

BACKGROUND OF THE INVENTION

Field of the Invention

The invention generally relates to recombinant vectors for use in cancer therapy and/or diagnostics, and to transgenic mice genetically engineered with one version of the vector. In particular, the invention provides vectors in which expression of one or more elements (e.g. genes required for viral replication, detectable imaging agents, therapeutic agents, etc.) is driven by a truncated CCN1 cancer selective promoter (tCCN1-Prom), Background of the Invention Cancer (malignant neoplasia) is a broad group of diseases involving unregulated cell growth. In cancer, cells divide and grow uncontrollably, forming malignant tumors, which may invade nearby parts of the body. The cancer may also spread to more distant parts of the body through the lymphatic system or bloodstream.

Cancer is usually treated with one or a combination of chemotherapy, radiation therapy and surgery. While treatment methods have advanced significantly, the outcomes for particular cancers are still not optimal, current treatments often have very harsh side effects, and if the cancer is not detected early, the chances of survival are greatly reduced.

Cancer can be detected in a number of ways, including the presence of certain signs and symptoms, various screening tests, and/or medical imaging. While detection methods have also improved markedly over the years, there is still a need in the art to detect and treat cancers earlier and more effectively. In particular, there is a great need to develop targeted therapeutic and imaging methodology so that e.g., tumors and metastatic cancer cells can be located and eliminated with a minimum of damage to healthy tissue. To that end, it would be advantageous to have available additional cancer-selective promoters in order to develop improved therapeutic and diagnostic constructs for use in the detection and treatment of cancers.

SUMMARY OF THE INVENTION

Recombinant vectors for use in cancer therapy and/or diagnostics, and in efficient "theranostics" (combined therapy and diagnostics) are described herein. The vectors advantageously contain at least one truncated CCN1 cancer-selective promoter (tCCN1-Prom) that is operationally linked to and drives expression of at least one element in the construct, e.g. expression of a therapeutic molecule, a molecule useful for diagnostics, or, when the vector is a viral vector, one or more genes that are necessary for replication of the vector, etc. In one aspect, the present disclosure describes exemplary uses of the tCCN1-Prom to produce "Cancer Terminator Viruses" (CTVs), recombinant adenoviruses that have profound therapeutic and/or therapeutic plus imaging potential in a broad spectrum of cancers; and to generate transgenic "CanView" and "MetaView" mice that can be used to follow tumor development, metastasis development and to monitor therapy efficacy and outcomes, e.g. by bioluminescence (BLI) in vivo.

Other features and advantages of the present invention will be set forth in the description of the invention that follows, and in part will be apparent from the description or may be learned by practice of the invention. The invention will be realized and attained by the compositions and methods particularly pointed out in the written description and claims hereof.

It is an object of this invention to provide a recombinant vector comprising a truncated CCN1 cancer selective promoter having a nucleotide sequence as set forth in SEQ ID NO: 1, or an active variant thereof. In some aspects, the truncated CCN1 cancer selective promoter is operably linked to at least one first gene of interest, e.g. a transgene. The recombinant vector may further comprise at least one promoter that is not truncated CCN1 and is also (like the truncated CCN1) operably linked to at least one additional gene of interest (usually a transgene that is generally not the same as the first gene of interest i.e. is generally different than the first gene of interest, e.g. a second, third, fourth, or more [e.g. 5th, 6th, 7th, 8th, 9th, 10th, etc.] gene of interest). In some aspects, the recombinant vector is a viral vector, with exemplary viral vectors being adenoviral vectors, lentiviral vectors, herpes simplex viral vectors, measles virus vectors, and vaccinia virus vectors. In some aspects, the at least one gene of interest encodes one or more of an anticancer agent, an imaging agent and at least one gene that is required for viral replication. Any of these described recombinant vectors may be present in a female transgenic mouse.

The invention further provides a cell (such as a cancer cell or a non-cancerous cell) comprising a recombinant truncated CCN1 cancer selective promoter having a nucleotide sequence as set forth in SEQ ID NO: 1, or an active variant thereof. Further aspects of the invention provide cells comprising a recombinant vector comprising a truncated CCN1 cancer selective promoter having a nucleotide sequence as set forth in SEQ ID NO: 1, or an active variant thereof. In some aspects, the truncated CCN1 cancer selective promoter is operably linked to at least one gene of interest. The recombinant vector may further comprise at least one promoter that is not truncated CCN1 and is also (like the truncated CCN1) operably linked to at least one gene of interest. In some aspects, the recombinant vector is a viral vector with exemplary viral vectors being adenoviral vectors, lentiviral vectors, herpes simplex viral vectors, measles virus vectors, and vaccinia virus vectors. In some aspects, at least one gene of interest encodes one or more of an anticancer agent, an imaging agent and at least one gene that is required for viral replication. The cells may be present in a female transgenic mouse or an organ or tissue of a female transgenic mouse, or may have been removed from a female transgenic mouse. In some aspects, the cells are cancer cells.

The invention also provides a female transgenic mouse, and offspring thereof, comprising a transgene under operational control of a cancer selective truncated CCN1 promoter. In some aspects, the transgene encodes a detectable imaging agent.

The invention further provides a female compound transgenic mouse, or offspring thereof, comprising i) a transgene under operational control of a cancer selective truncated CCN1 promoter, wherein said transgene encodes a detectable imaging agent, and ii) a transgene or genetic mutation that renders the female compound transgenic mouse prone to develop cancer and/or metastatic cancer.

The invention also provides methods of non-invasively imaging cancer cells and metastases in a female transgenic mouse that develops cancer, comprising i) providing a transgenic mouse by genetically engineering a mouse to contain and express a detectable imaging agent under operational control of a cancer selective truncated CCN1 promoter; ii) providing at least one female compound transgenic mouse by breeding the transgenic mouse provided in step i) to a mouse that is genetically prone to develop cancer; and iii) non-invasively imaging cancer cells in said at least one female compound transgenic mouse by detecting expression of said detectable imaging agent in cancer cells of said at least one female compound transgenic mouse. In some aspects, the method further comprises the steps of, if cancer cells are detected in said detecting step, administering a candidate or putative anti-cancer agent to said compound transgenic mouse; then repeating the step of detecting cancer cells; and, if no or fewer cancer cells are detected in said repeating step than were detected in said detecting step, then, concluding that said candidate anti-cancer agent is an effective anti-cancer agent; and/or if cancer cells are detected in said detecting step, administering a candidate anti-cancer agent to said compound transgenic mouse; then repeating said step of detecting cancer cells; and, if the same or more cancer cells are detected in said repeating step than in said first detecting step, then, concluding that said candidate anti-cancer agent is not an effective anti-cancer agent. In yet other aspects, the method further comprises the steps of; if cancer cells are not detected in said female transgenic mouse, administering a candidate anti-cancer agent to said compound female transgenic mouse; repeating said step of detecting cancer cells after a time period during which said transgenic mouse would normally develop cancer; and, if no cancer cells are detected in said repeating step or if fewer cancer cells are detected in said repeating step than would be predicted in the absence of said candidate anti-cancer cancer agent, then, concluding that said candidate anti-cancer agent is an effective cancer prevention agent.

The invention also provides methods of treating and/or preventing and/or imaging cancer in a patient in need thereof, comprising administering to said patient a composition comprising one or more recombinant vectors as described above. In some aspects, the cancer that is treated is breast, cervical, endometrial, gestational trophoblastic disease, ovarian cancer, uterine sarcoma, vaginal and vulvar. Also provides are methods of monitoring the progress and outcome of the treatment methods, and of adjusting treatment regiments in view of results obtained during monitoring.

BRIEF DESCRIPTION OF THE DRAWINGS

FIGS. 1A and B. tCCN1 promoter activity in Prostate cancer (PC) and cloned rat embryo fibroblast (CREF) series of cell lines. A. Prostate cancer DU-145, PC-3, ARCaP, ARCaP-E, and ARCaP-M cells and normal RWPE-1 and P69 cells were transfected with pGL3-luc reporter vector driven by PEG-Prom (pPEG-luc) or tCCN1-Prom (pCCN1-luc). pRL-TK (Renilla luciferase) was co-transfected for the normalization of luciferase activity, and the luminescence readings were plotted as relative luminescence units (RLU). *($p<0.05$), ($p<0.01$) and *($p<0.001$) indicates the statistical significance by using t-test between pPEG-luc and pCCN1-luc transfected cells. B. src-, raf-, ras- and HPV-transformed CREF cells were treated with p-CCN1-luc and/or TPA (200 ng/ml). The results were recorded as RLU. *($p<0.05$) and **($p<0.01$) indicates the statistical significance between pCCN1-luc and pCCN1-luc plus TPA treated cells.

FIG. 10. Nucleotide sequence of tCCN1 promoter.

DETAILED DESCRIPTION

Figure 2A:
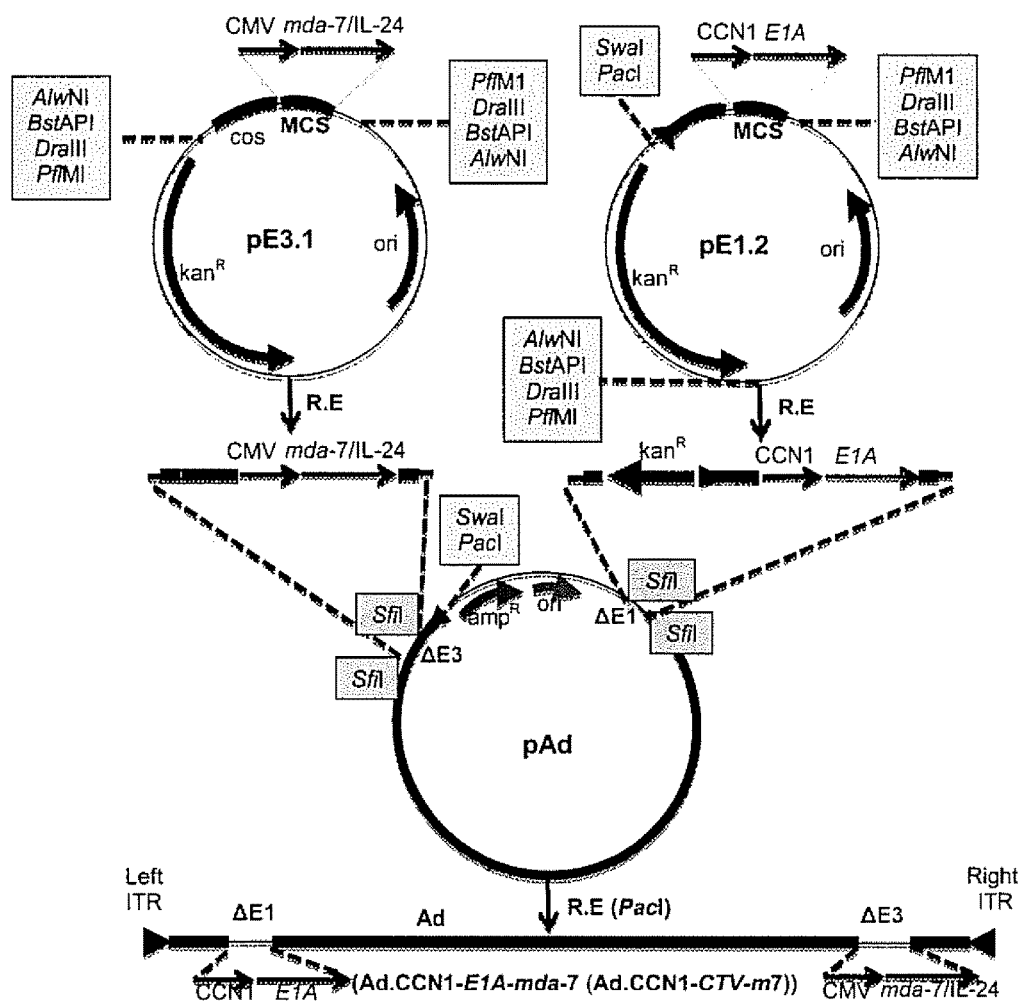
FIGS. 2A and B. Conditionally cancer-specific replication competent bipartite Cancer Terminator Virus (CTV) driven by tCCN1-Prom (Ad.CCN1-CTV-m7) replicates and simultaneously produces mda-7/IL-24 in prostate cancer cells. A, Schematic representation of tCCN1-CTV-m7 or Ad.CCN1-CTV-m7 (Ad.CCN1-E1A-mda-7). In Ad.CCN1-E1A-mda-7, the tCCN1-Prom regulating the expression of E1A and E1B genes was placed in the deleted region of the E1A and E1B region (ΔE1) of pAd and CMV-Prom regulating the expression of mda-7/IL-24 was inserted in the deleted region of E3 (ΔE3) of pAd using two-shuttle vectors pE3.1 and pE1.2. This CTV or Ad.CCN1-CTV-m7 does not harm normal cells but induces oncolysis by Ad replication and diverse tumor-suppressor effects of the expressed transgene mda-7/IL-24. B, MDA-7/IL-24 protein expression in conditioned medium of prostate cancer cells and normal human immortalized prostate epithelial cells RWPE-1 after infection with Ad.mda-7 (100 vp/cell) and Ad.CCN1-CTV-m7 (100 vp/cell) as measured by human IL-24 ELISA kit.

The CCN1 promoter is an immediate early response gene regulated transcriptionally in a protein kinase C (PKC)-, cyclic AMP-responsive element binding protein (CREB)-, and AP-1-dependent manner in various cell lines [1-4]. Previously it was shown that cyclic AMP is higher in prostate and breast cancer cells as compared to normal epithelial cells of various origins, and thus higher expression of CCN1-prom and subsequently CCN1 protein is expected in cancer cells [1]. CCN1/Cry61 displays elevated expression as a function of oncogenic transformation in various cancers including prostate, pancreas and breast [1, 5, 6], and expression increases with aggressiveness of the transformed phenotype [5, 7, 8].

A ~830-kb fragment of the CCN1 promoter (truncated CCN1 or "tCCN1", SEQ ID NO: 1) was cloned and its successful use to selectively drive expression of genes of interest in cancer cells in a variety of scenarios (e.g. diagnostics, therapeutics and combinations thereof) is described herein. As shown in the Examples provided below, the tCCN1 promoter (tCCN1-Prom) displays selective elevated activity in a wide array of human cancers, with minimal activity in normal cells. tCCN1-Prom can thus be used to drive expression of one or more elements of interest in a wide variety of vectors and constructs that are useful for anti-cancer treatment, for cancer imaging and diagnostics, and for combined cancer therapy and imaging applications ("theranostics"). To that end, the disclosure describes exemplary vectors such as adenoviral vectors (which may be referred to herein as "Cancer Terminator Viruses" or "CTVs"), which replicate selectively in cancer cells. In some aspects, the CTVs simultaneously produce a therapeutic cytokine (for example, mda-7/IL-24) and/or genes necessary for adenoviral replication, with expression being driven by tCCN1-Prom and one additional promoter. In one type of non-limiting, exemplary "bipartite" adenovirus, the E1A/E1B genes of adenovirus are under transcriptional regulation of the tCCN1-Prom and expression of the anti-cancer agent mda-7/IL-24 is controlled by a different promoter, e.g. the non-selective constitutive CMV promoter As described herein, this type of construct shows selective activity in inducing toxicity (apoptosis) uniquely in human prostate and other cancer cells, both in vitro and in vivo in nude mice. In addition, vectors and constructs which contain two or more tCCN1-Proms each driving expression of a gene or other element of interest, with or without additional promoters driving expression of other genes or other elements of interest, are also encompassed. However, to potentially avoid recombination, generally only one tCCN1-Prom is used per construct, together with one or more additional cancer-specific (e.g. PEG-Prom) or cancer-selective (e.g. hTERT) promoters or non-cancer specific/selective promoters. In an exemplary "tripartite" virus three promoters (tCCN1-Prom, PEG-Prom and CMV-Prom) are utilized.

Based on the demonstrated cancer-cell selectivity of the constructs described herein, the efficacy of the tCCN1-Prom with respect to imaging was tested in a construct (CCN1-Prom-luc) in which tCCN1-Prom drove the expression of the luciferase gene. Surprisingly, since it is not a full length, native or naturally occurring promoter, CCN1-Prom-luc was found to have the ability to express luciferase selectively in tumors and to advantageously permit imaging of metastases when administered to tumor/metastasis containing nude mice.

In addition, female transgenic mice in which tCCN1-Prom-luc is present in all tissues of the mice have been constructed and tested. Female transgenic mice do not show any background luminescence, and when crossed with MMTV-PyMT mice, which develop primary and metastatic mammary tumors, successful imaging of tumor development and metastases in the animals was carried out using a bioluminescence (BLI) approach. This novel mouse model is useful for a variety of applications, including as an investigational tool e.g. to follow or monitor cancer development and progression, and to monitor and assess the effect of therapeutic intervention or other factors on cancer development and/or metastases.

Definitions

PEG-Prom: progression elevated gene-3 (PEG-3) promoter
luc: luciferase
CREF cells: cloned Fischer rat embryo fibroblast cells (immortal rat embryo fibroblast cell line that is contact inhibited and does not form tumors in nude mice)

Ad: adenovirus
PC: prostate cancer
CRCA: conditionally replication competent adenovirus
MMTV-PyMT mice express the mouse polyomavirus middle-T antigen (PyMT) under the control of the mouse mammary tumor virus (MMTV) long terminal repeat. These transgenic animals uniformly develop multi focal mammary tumors with a high incidence of pulmonary metastasis.
Theranostic: construct comprising both one or more therapeutic agents and one or more diagnostic agents,
Transgene: a gene that is taken from the genome of one organism and introduced into another host organism by artificial (e.g. genetic engineering) techniques. The two organisms may or may not be of the same species and the transgene may or may not be modified from its original form prior to introduction into the host organism.
tCCN1-Prom The nucleotide sequence of tCCN1-Prom is presented in FIG. 10 as SEQ ID NO: 1. However, as used herein "tCCN1-Prom" also includes various variant nucleotide sequences having at least about 50, 55, 60, 65, 70, 76, 80, 85, 90, 95, 96, 97, 98, or 99% identity to SEQ ID NO:1, so long as the nucleotide substitutions in such variant sequences do not impair the function/activity of the promoter, or at least as long as at least about 50, 55, 60, 65, 70, 76, 80, 85, 90, 95 or 100% of the activity is retained. In some aspects, the activity of a variant may exceed that of the sequence shown in SEQ ID NO: 1.

In addition to substitutions, various deletions and/or additions of nucleotides may be tolerated, or even advantageous, e.g. deletions of from about 1-100 nucleotides (e.g. about 5, 10, 20, 25, 30, 35, 40, 45, 50, 55, 60, 65, 70, 75, 80, 85, 90, 95 or 100 nucleotides), or insertions of about 1-100 nucleotides (e.g. about 5, 10, 20, 25, 30, 35, 40, 45, 50, 55, 60, 65, 70, 75, 80, 85, 90, 95 or 100 nucleotides), may occur throughout the sequence, so long as promoter activity is not impaired or decreased outside the limits listed above. All such variant promoters are encompassed by the invention. Deletions and insertions may be internal or at the 3' or 5' ends of the sequence. "Insertions" may result in what is essentially a full-length CCN1 promoter, or a recombinant promoter that is intermediate in length between full-length CCN1 and tCCN1 as described herein, or "deletions" may result in an active promoter that is shorter than the tCCN1 that is disclosed herein, having e.g. at least about 500, 550, 600, 650, 700, 750 or 800 base pairs. For the tCCN1 promoter and all variants thereof, when present in a construct as described herein, the sequence of the promoter is flanked, at either or both of the 3' and 5' termini, by at least one nucleotide or nucleotide sequence that is not present at that position in nature, i.e. the nucleotide or sequence is heterologous or non-native. In some aspects, a tCCN1 promoter sequence may be an isolated sequence, i.e. not connected or embedded within a larger nucleotide sequence. Primers specific for amplifying the tCCN1 promoters described herein are also encompassed by the invention.

Vectors and Other Constructs and/or Carriers

Herein, the terms "construct" and "vector" refer to a recombinant nucleic acid molecules that contains at least one tCCN1 promoter, usually operably linked to a nucleotide sequence (e.g. a transgene) that encodes a product of interest, which may be a protein or polypeptide, with which the promoter is not linked in nature (e.g. a heterologous transgene). However, nanoparticles containing such nucleic acids may also be included within this meaning, as may liposomes and other types of vehicles, which contain or house and are used to deliver nucleic acids. Constructs and vectors are generally made or manufactured using genetic engineering or other laboratory techniques. The terms may be used interchangeably herein.

Vectors that may be used in the practice of the invention include both viral and non-viral vectors. Exemplary non-viral vectors that may be employed include but are not limited to, for example: cosmids or plasmids; and, particularly for cloning large nucleic acid molecules, bacterial artificial chromosome vectors (BACs) and yeast artificial chromosome vectors (YACs); as well as liposomes (including targeted liposomes); cationic polymers; ligand-conjugated lipoplexes; polymer-DNA complexes; poly-L-lysine-molossin-DNA complexes; chitosan-DNA nanoparticles; polyethylenimine (PEI, e.g. branched PEI)-DNA complexes; various nanoparticles and/or nanoshells such as multifunctional nanoparticles, metallic nanoparticles or shells (e.g. positively, negatively or neutral charged gold particles, cadmium selenide, etc.); ultrasound-mediated microbubble delivery systems; various dendrimers (e.g. polyphenylene and poly(amidoamine)-based dendrimers; etc.

In addition, viral vectors may be employed. Exemplary viral vectors include but are not limited to: bacteriophages, various baculoviruses, retroviruses, and the like. Those of skill in the art are familiar with viral vectors that are used in "gene therapy" applications, which include but are not limited to: herpes simplex virus vectors (Geller et al., Science, 241:1667-1669 (1988)); vaccinia virus vectors (Piccini et al., Meth. Enzymology, 153:545-563 (1987)); cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., Proc. Natl. Acad. Sci. USA, 85:6460-6464 (1988); Blaese et al., Science, 270:475-479 (1995); Onodera et al., J. Virol., 72:1769-1774 (1998)); adenovirus vectors (Berkner, Biotechniques, 6:616-626 (1988); Cotten et al., Proc. Natl. Acad. Sci. USA, 89:6094-6098 (1992); Graham et al., Meth. Mol. Biol., 7:109-127 (1991); Li et al., Human Gene Therapy, 4:403-409 (1993); Zabner et al., Nature Genetics, 6:75-83 (1994)); adeno-associated virus vectors (Goldman et al., Human Gene Therapy, 10:2261-2268 (1997); Greelish et al., Nature Med., 5:439-443 (1999); Wang et al., Proc. Natl. Acad. Sci. USA, 96:3906-3910 (1999); Snyder et al., Nature Med., 5:64-70 (1999); Herzog et al., Nature Med., 5:56-63 (1999)); retrovirus vectors (Donahue et al., Nature Med., 4:181-186 (1998); Shackleford et al., Proc. Natl. Acad. Sci. USA, 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., Nature Genetics, 17:314-317 (1997), as well as viruses that are replication-competent conditional to a cancer cell such as oncolytic herpes virus NV 1066 and vaccinia virus GLV-1h68, as described in United States patent application 2009/0311664. In particular, adenoviral vectors may be used, e.g. targeted viral vectors such as those described in published United States patent application 2008/0213220.

Those of skill in the art will recognize that the choice of a particular vector will depend on the details of its intended use. Typically, one would not use a vector that integrates into the host cell genome due to the risk of insertional mutagenesis, and would design vectors so as to avoid or minimize the occurrence of recombination within a vector's nucleic acid sequence or between vectors. However, if for any reason host cell chromosomal integration is desired, vectors such as retroviral vectors may be employed.

Host cells which contain the recombinant tCNN1 promoter or vectors containing the promoter are also encompassed, e.g. in vitro cells such as cultured cells, or bacterial or insect cells which are used to store, generate or manipulate the vectors, and the like. The constructs and vectors may be produced using known recombinant technology or by synthetic (e.g. chemical) means.

Promoters that May be Used with tCCN1 in Constructs

The constructs and vectors described herein contain at least one copy of a tCCN1 promoter that is operably linked to a gene of interest. "Operably linked" refers to the promoter being located or positioned within a recombinant construct so as to interact with a nucleotide sequence encoding a gene of interest in a manner that results in successful transcription of the nucleic acid. Other genetic elements such as enhancers may also be present in the construct and may participate in transcription.

The constructs may also include one or more other promoters, each of which is operably linked to a gene of interest, usually a gene of interest that differs from the gene of interest that is operably linked to the tCCN1-Prom, although this may not always be the case. Depending on the overall design, the additional promoters may or may not be specific or selective (preferential) for driving expression within cancer cells, and may be inducible or constitutive. Exemplary suitable cancer selective/specific promoters (and or promoter/enhancer sequences) that may be used include but are not limited to: PEG-PROM (e.g. as described in U.S. patent application Ser. No. 13/881,777), astrocyte elevated gene 1 (AEG-1) promoter, survivin-Prom, human telomerase reverse transcriptase (hTERT)-Prom, hypoxia-inducible-1-alpha (HIF-1-alpha)-Prom, Growth arrest and DNA damage (GADD) inducible promoters (e.g. GADD-Prom), metastasis-associated promoters (metalloproteinase, collagenase, etc.), ceruloplasmin promoter (Lee et al., Cancer Res Mar. 1, 2004 64; 1788), mucin-1 promoters such as DF3/MUC1 (see U.S. Pat. No. 7,247,297), HexII promoter as described in US patent application 2001/00111128; prostate-specific antigen enhancer/promoter (Rodriguez et al. Cancer Res., 57: 2559-2563, 1997); melanoma-specific promoter Tyrex2chimeric promoter; α-fetoprotein gene promoter (Hallenbeck et al. Hum. Gene Ther., 10: 1721-1733, 1999); the surfactant protein B gene promoter (Doronin et al. 3. Virol., 75: 3314-3324, 2001); MUC1 promoter (Kurihara et al. J. Clin. Investig., 106: 763-771, 2000); H19 promoter as per U.S. Pat. No. 8,034,914; those described in issued U.S. Pat. Nos. 7,816,131, 6,897,024, 7,321,030, 7,364,727, and others; etc., as well as derivative forms thereof. Any promoter that is specific or selective for driving gene expression in cancer cells, or in cells of a particular type of cancer (so as to treat e.g. prostate, colon, breast, etc. primary and metastatic cancer) may be used in the practice of the invention. By "specific for driving gene expression in cancer cells" we mean that the promoter, when operably linked to a gene, functions to promote transcription of the gene only when located within a cancerous, malignant cell, but not when located within normal, non-cancerous cells. By "selective for driving gene expression in cancer cells" we mean that the promoter, when operably linked to a gene, functions to promote transcription of the gene to a greater degree when located in within a cancer cell, than when located within non-cancerous cells. For example, the promoter drives gene expression of the gene at least about 2-fold, or about 3-, 4-, 5-, 6-, 7-, 8-, 9-, or 10-fold, or even about 20-, 30-, 40-, 50-, 60-, 70-, 80-, 90- or 100-fold or more (e.g. 500- or 1000-fold) when located within a cancerous cell than when located within a non-cancerous cell, when measured using standard gene expression measuring techniques that are known to those of skill in the art.

Additional promoters (including tissue or cell selective and/or specific, and non-selective/non-specific promoters) include but are not limited to: neuroendocrine cell-specific and neuroendocrine cell-preferential promoters, SIRT1, IRF6, SV40 IE, RSV LTR, GAPDH, ubiquitin, bovine papilloma virus or polyoma, RIP1, multimerized RIP and HIP promoters (e.g. CMV), murine molony leukemia virus (MMLV-LTR) promoter, mouse tumor virus promoter, avian sarcoma virus promoter, adenovirus II promoters, e.g. the Ad2 major late promoter (Ad2 MLP), tyrosinase promoter, melanoma inhibitory activity (MIA) promoter, melanocortin 1 receptor (receptor MC1R, cyclooxygenase 2 (Cox-2) promoter, CXCR4, and BIRC5 SV40 and CMV promoters, CMV-hTERT (a chimeric double promoter based on promoters of the hASH1 and EZH2 genes), etc.

The transcriptional elements may include other transcription or translation supporting elements such as enhancers, regulatory elements, response elements, etc. and the promoters may be heterologous (not associated with the encoded gene of interest in nature) or homologous (associated with the encoded gene of interest in nature).

Exemplary Genes and Elements of Interest that May be Expressed Using Truncated CCN1 Alone or in Combination with Other Promoters A variety of molecules may be expressed under control of a tCCN1 promoter and/or under control of other promoters that are used in combination with tCCN1-Prom in a construct In some aspects, a gene encoding a therapeutic molecule, e.g. a protein or polypeptide, which is deleterious to cancer cells, is operably linked to a promoter as described herein, e.g. a cancer-specific or selective promoter. The therapeutic protein may kill cancer cells (e.g. by initiating or causing apoptosis), or may slow their rate of growth (e.g. may slow their rate of proliferation), or may arrest their growth and development or otherwise damage the cancer cells in some manner, or may even render the cancer cells more sensitive to other anti-cancer agents, etc.

Genes encoding therapeutic molecules that may be employed as described herein include but are not limited to suicide genes, including genes encoding various enzymes; oncogenes; tumor suppressor genes; toxins; cytokines; oncostatins; TRAIL, etc. Exemplary enzymes include, for example, thymidine kinase (TK) and various derivatives thereof; TNF-related apoptosis-inducing ligand (TRAIL), xanthine-guanine phosphoribosyltransferase (GPT); cytosine deaminase (CD); hypoxanthine phosphoribosyl transferase (HPRT); etc. Exemplary tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), AdE1A, and nm23. Suitable toxins include *Pseudomonas* exotoxin A and S; diphtheria toxin (DT); *E. coli* LT toxins, Shiga toxin, Shiga-like toxins (SLT-1, -2), ricin, abrin, supporin, gelonin, etc. Suitable cytokines include interferons and interleukins such as interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT, "M4" region of MDA-7/IL-24, and combinations thereof. Other anti-tumor agents include: GM-CSF interleukins, tumor necrosis factor (TNF); interferon-beta and virus-induced human Mx proteins; TNF alpha and TNF beta; human melanoma differentiation-associated gene-7 (mda-7), also known as interleukin-24 (IL-24), various truncated versions of mda-7/IL-24 such as M4; siRNAs and shRNAs targeting important growth regulating or oncogenes which are required by or overexpressed in cancer cells; antibodies such as antibodies that are specific or selective for attacking cancer cells; etc.

When the therapeutic agent is TK (e.g. viral TK), a TK substrate such as acyclovir, ganciclovir, or various thymidine analogs (e.g. those containing o-carboranylalkyl groups at the 3-position [Cancer Res Sep. 1, 2004 64; 6280]) is administered to the subject. These drugs act as prodrugs, which in themselves are not toxic, but are converted to toxic drugs by phosphorylation by viral TK. Both the TK gene and substrate must be used concurrently to be toxic to the host cancer cell.

Exemplary Applications of the Truncated Promoter

The tCCN1 promoter displays elevated cancer-selective activity in a wide array of human cancers, with minimal activity in normal cells. To further extend its usefulness, a Cancer Terminator Virus (CTV) was generated which replicates selectively in cancer cells and simultaneously produces a therapeutic cytokine (in this case mda-7/IL-24). In this bipartite adenovirus the E1A/E1B genes of adenovirus are under the transcriptional regulation of the tCCN1-Prom and mda-7/IL-24 expression is controlled by the CMV-Prom (Ad.CCN1-E1A-mda-7; Ad.CCN1-CTV-m7). This virus shows selective activity in inducing toxicity (apoptosis) uniquely in human prostate and other cancer cells, both in vitro and in vivo in nude mice as well as in immunocompetent mice using a microbubble delivery system to shield Ads from the immune system and restrict trapping in the liver. Based on its cancer-cell selectivity, the efficacy of the tCCN1-Prom in the context of imaging was also tested. tCCN1-Prom-luc, tCCN1-Prom driving luciferase activity, was tested and found to have the ability to image tumors and particularly metastases when administered to tumor/metastasis bearing nude mice. Transgenic mice were also constructed in which the tCCN1-Prom is present in all tissues of the mice. Female transgenic mice of this type do not show any background luminescence, but when crossed with MMTV-PyMT mice, which develop primary and metastatic mammary tumors, imaging of primary tumor and metastases in these animals is evident by using bioluminescence (BLI) approach. This novel CanView or MetView mouse model can be used to follow cancer development and progression to metastasis and/or the effects of therapeutic intervention.

Therapy and Administration

Targeted cancer therapy is carried out by administering the constructs, vectors, etc. which encode one or more copies of a recombinant vector containing a tCNN1 promoter as described herein to a patient in need thereof. The vector compositions (preparations) of the present invention are typically administered systemically, although this need not always be the case, as localized administration (e.g. intratumoral, peritumoral, or into an external orifice such as the vagina, the nasopharyngeal region, the mouth; or into an internal cavity such as the thoracic cavity, the cranial cavity, the abdominal cavity, the spinal cavity, etc.) is not excluded. For systemic distribution of the vector, the preferred routes of administration include but are not limited to: intravenous, by injection, transdermal, via inhalation or intranasally, or via injection or intravenous administration of a cationic polymer-based vehicle (e.g. in vivo-jetPEI™). Liposomal delivery, which when combined with targeting moieties will permit enhanced delivery. The ultrasound-targeted microbubble-destruction technique (UTMD) may also be used to deliver imaging and theranostic agents (Dash et al. Proc Natl Acad Sci USA. 2011 May 24; 108(21):8785-90. Epub 2011 May 9]; as may hydroxyapatite-chitosan nanocomposites (Venkatesan et al. Biomaterials. 2011 May; 32(151:3794-806); and others (Dash et al. Discov Med. 2011 January; 11(56):46-56. Review); etc. Any method that is known to those of skill in the art, and which is commensurate with the type of construct that is employed, may be utilized.

Those of skill in the art will recognize that the amount of a construct or vector that is administered will vary from patient to patient, and possibly from administration to administration for the same patient, depending on a variety of factors, including but not limited to: weight, age, gender, overall state of health, the particular disease being treated, and other factors, and that the amount and frequency of administration is best established by a health care professional such as a physician or oncologist. Typically, optimal or effective tumor-inhibiting or tumor-killing amounts are established e.g. during animal trials and during standard clinical trials. Those of skill in the art are familiar with conversion of doses e.g. from a mouse to a human, which is generally done through body surface area, as described by Freireich et al. (Cancer Chemother Rep 1966; 50(4):219-244); and see Tables 1 and 2 below, which are taken from the website located at dtp.nci.nih.gov.

TABLE 1

Conversion factors in mg/kg

|  | Mouse wt. 20 g | Rat wt 150 g | Monkey wt 3 kg | Dog wt 8 kg | Human wt 60 kg |
|---|---|---|---|---|---|
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 1 2/3 | 1 | 1/2 |

For example, given a dose of 50 mg/kg in the mouse, an appropriate dose in a monkey would be 50 mg/kg×¼=13 mg/kg/; or a dose of about 1.2 mg/kg is about 0.1 mg/kg for a human.

TABLE 2

Representative Surface Area to Weight Ratios

| Species | Body Weight (kg) | Surface Area (sq. m.) | Km factor |
|---|---|---|---|
| Mouse | 0.02 | 0.0066 | 3.0 |
| Rat | 0.15 | 0.025 | 5.9 |
| Monkey | 3.0 | 0.24 | 12 |
| Dog | 8.0 | 0.4 | 20 |
| Human, child | 20 | 0.8 | 25 |
| Human, adult | 60 | 1.6 | 37 |

To express the dose as the equivalent mg/sq.m. dose, multiply the dose by the appropriate factor. In adult humans, 100 mg/kg is equivalent to 100 mg/kg×37 kg/sq.m.=3700 mg/sq.m.

In general, for treatment methods, the amount of a vector such as a plasmid will be in the range of from about 0.01 to about 5 mg/kg or from about 0.05 to about 1 mg/kg (e.g. about 0.1 mg/kg); and/or from about $10^5$ to about $10^{20}$ infectious units (IUs), or from about $10^8$ to about $10^{13}$ IUs for a viral-based vector. in general, for therapy plus imaging methods, the amount of a vector will be in the range of from about 0.01 to about 5 mg/kg or from about 0.05 to about 1 mg/kg (e.g. about 0.1 mg/kg) of e.g. a plasmid, and from about $10^5$ to about $10^{20}$ infectious units (IUs), or from about $10^8$ to about $10^{13}$ IUs for a viral-based vector. Those of skill in the art are familiar with calculating or determining the level of an imaging signal that is required for adequate detection. For example, for radiopharmaceuticals such as [124I]FIAU, an injection on the order or from about 1 mCi to about 10 mCi, and usually about 5 mCi, (i.e. about 1 mg of material) is generally sufficient.

Further, one type of vector or more than one type of vector may be administered in a single administration, e.g. a therapy vector plus an imaging vector, or two (or more) different therapy vectors (e.g. each of which have differing modes of action so as to optimize or improve treatment outcomes), or two or more different imaging vectors, etc.

Typically cancer treatment requires repeated administrations of the compositions. For example, administration may be daily or every few days, (e.g. every 2, 3, 4, 5, or 6 days), or weekly, bi-weekly, or every 3-4 weeks, or monthly, or any combination of these, or alternating patterns of these. For example, a "round" of treatment (e.g. administration once a week for a month) may be followed by a period of no administration for a month, and then followed by a second round of weekly administration for a month, and so on, for any suitable period of time, as required to optimally treat the patient.

In addition, the compositions may be administered in conjunction with other treatment modalities known in the art, such as various chemotherapeutic agents such as Pt drugs and other chemotherapy agents, radiation therapy, substances that boost the immune system, antibiotic agents, and the like; and/or with detection and imaging methods (e.g. in conjunction with mammograms, X-rays, Pap smears, prostate specific antigen (PSA) tests, etc.

The subjects or patients to whom the compositions of the invention are administered are typically mammals, frequently humans, but this need not always be the case. Veterinary applications are also contemplated.

Imaging Plus Treatment

In some embodiments, the invention provides cancer treatment protocols in which treating the disease, e.g. killing, destroying, or otherwise damaging the cancer cells, is combined with imaging of cancer cells and tumors. These protocols may be referred to herein as "theranostics" or "combined therapies" or "combination protocols", or by similar terms and phrases.

In some aspects, the combined therapy involves administering to a cancer patient a vector that encodes, in a single construct, both a tCCN1 promoter and at least one additional promoter, one of which drives expression of a therapeutic molecule (e.g. mda-7) and the other of which drives expression of a reporter gene (for imaging). In addition, one or more genes that are otherwise necessary for the vector or construct to perform its function may be expressed, e.g. by yet another promoter. In this embodiment, expression of one or more of the genes is generally mediated by a cancer cell specific or selective promoter such as tCCN1. Preferably, at least two different promoters are used in this embodiment in order to prevent or lessen the chance of crossover and recombination within the construct. Alternatively, tandem translation mechanisms may be employed, for example, the insertion of one or more internal ribosomal entry site (IRES) into the construct, which permits translation of multiple mRNA transcripts from a single mRNA. In this manner, both at least one reporter protein/polypeptide and at least one therapeutic protein/polypeptide that is lethal or toxic to cancer cells, and, optionally one or more vector-related genes (such as adenoviral structural genes) are selectively or specifically produced within the targeted cancer cells.

Alternatively, the polypeptides encoded by the constructs of the invention (e.g. plasmids, viral vectors, etc.) may be genetically engineered to contain a contiguous sequence comprising a reporter and a therapeutic gene separated by an intervening sequence that is cleavable within the cancer cell, e.g. a sequence that is enzymatically cleaved by intracellular proteases, or even that is susceptible to non-enzymatic hydrolytic cleavage mechanisms. In this case, cleavage of the intervening sequence results in production of functional polypeptides, i.e. polypeptides which are able to carry out their intended function, e.g. they are at least 50, 60, 70, 80, 90, or 100% (or possible more) as active as the protein sequences on which they are modeled or from which they are derived, when measured using standard techniques that are known to those of skill in the art.

In other aspects of combined imaging and therapy, two different vectors may be administered, one of which is an "imaging vector or construct" as described herein, and the other of which is a "therapeutic vector or construct" as described herein. At least one of the vectors comprises a tCCN1-Prom.

In other aspects of combined imaging and therapy, the genes of interest are encoded in the genome of a viral vector that is capable of transcription and/or translation of multiple mRNAs and/or the polypeptides or proteins they encode, by virtue of the properties inherent in the virus. In this embodiment, such viral vectors are genetically engineered to contain and express genes of interest (e.g. both a reporter gene and at least one therapeutic gene) under the principle control of one or more cancer specific promoters, at least one of which is tCCN1.

In the "therapy plus imaging" aspect of the invention, the vectors/constructs include at least one transcribable element that is either directly detectable using imaging technology, or which functions with one or more additional molecules in a manner that creates a signal that is detectable using imaging technology. The transcribable element is operably linked to a promoter, which may be a cancer selective/specific promoter as described above, and is generally referred to as a "reporter" molecule. Reporter molecules can cause production of a detectable signal in any of several ways: they may encode a protein or polypeptide that has the property of being detectable in its own right; they may encode a protein or polypeptide that interacts with a second substance and causes the second substance to be detectable; they may encode a protein or polypeptide that sequesters a detectable substance, thereby increasing its local concentration sufficiently to render the surrounding environment (e.g. a cancer cell) detectable. If the gene product of the reporter gene interacts with another substance to generate a detectable signal, the other substance is referred to herein as a "complement" of the reporter molecule.

Examples of reporter proteins or polypeptides that are detectable in their own right (directly detectable) include those which exhibit a detectable property when exposed to, for example, a particular wavelength or range of wavelengths of energy. Examples of this category of detectable proteins include but are not limited to: green fluorescent protein (GFP) and variants thereof, including mutants such as blue, cyan, and yellow fluorescent proteins; proteins which are engineered to emit in the near-infrared regions of the spectrum; proteins which are engineered to emit in the short-, mid-, long-, and far-infrared regions of the spectrum; etc. Those of skill in the art will recognize that such detectable proteins may or may not be suitable for use in humans, depending on the toxicity or immunogenicity of the reagents involved. However, this embodiment has applications in, for example, laboratory or research endeavors involving animals, cell culture, tissue culture, various ex vivo procedures, etc.

Another class of reporter proteins is those that function with a complement molecule. In this embodiment, a construct comprising a gene encoding a reporter molecule is administered systemically to a subject in need of imaging, and a molecule that is a complement of the reporter is also administered systemically to the subject, before, after or together with the construct. If administered prior to or after administration of the construct, administration of the two may be timed so that the diffusion of each entity into cells, including the targeted cancer cells, occurs in a manner that results in sufficient concentrations of each within cancer cells to produce a detectable signal, e.g. typically within about 1 hour or less. If the two are administered "together", then separate compositions may be administered at the same or nearly the same time (e.g. within about 30, 20, 15, 10, or 5 minutes or less), or a single composition comprising both the construct and the complement may be administered. In any case, no interaction between the reporter and the complement can occur outside of cancer cells, because the reporter is not produced and hence does not exist in any other location, since its transcription is controlled by a cancer specific/selective promoter.

One example of this is the oxidative enzyme luciferase and various modified forms thereof, the complement of which is luciferin. Briefly, catalysis of the oxidation of its complement, luciferin, by luciferase produces readily detectable amounts of light. Those of skill in the art will recognize that this system is not generally used in humans due to the need to administer the complement, luciferin to the subject. However, this embodiment is appropriate for use in animals, and in research endeavors involving cell culture, tissue culture, and various ex vim procedures.

Another exemplary protein of this type is thymidine kinase (TK), e.g. TK from herpes simplex virus 1 (HSV 1), or from other sources, TK is a phosphotransferase enzyme (a kinase) that catalyzes the addition of a phosphate group from ATP to thymidine, thereby activating the thymidine for incorporation into nucleic acids, e.g. DNA. Various analogs of thymidine are also accepted as substrates by TK, and radiolabeled forms of thymidine or thymidine analogs may be used as the complement molecule to reporter protein TK, Without being bound by theory, it is believed that once phosphorylated by TK, the radiolabeled nucleotides are retained intracellularly because of the negatively charged phosphate group; or, alternatively, they may be incorporated into e.g. DNA in the cancer cell, and thus accumulate within the cancer cell. Either way, they provide a signal that is readily detectable and distinguishable from background radioactivity. Also, the substrate that is bound to TK at the time of imaging provides additional signal in the cancer cell. In fact, mutant TKs with very low Kms for substrates may augment this effect by capturing the substrate. The radioactivity emitted by the nucleotides is detectable using a variety of techniques, as described herein. This aspect of the use of TK harnesses the labeling potential of this enzyme; the toxic capabilities of TK are described below.

Various TK enzymes or modified or mutant forms thereof may be used in the practice of the invention, including but not limited to: HSV1-TK, HSV1-sr39TK, mutants with increased or decreased affinities for various substrates, temperature sensitive TK mutants, codon-optimized TK, the mutants described in U.S. Pat. No. 6,451,571 and US patent application 2011/0136221, both of which are herein incorporated by reference; various suitable human TKs and mutant human TKs, etc.

Detectable TK substrates that may be used include but are not limited to: thymidine analogs such as: "fialuridine" i.e. [1-(2-deoxy-2-fluoro-1-D-arabinofuranosyl)-5-iodouracil], also known as "FIAU" and various forms thereof, e.g. 2'-fluoro-2'-deoxy-β-D-5-[$^{125}$I]iodouracil-arabinofuranoside ([$^{12}$I] FIAU), [$^{124}$I] FIAU; thymidine analogs containing o-carboranylalkyl groups at the 3-position, as described by Al Mahoud et al., (Cancer Res Sep. 1, 2004 64; 6280), which may have a dual function in that they mediate cytotoxicity as well, as described below; hydroxymethyl]butyl)guanine (HBG) derivatives such as 9-(4-$^{18}$F-fluoro-3-[hydroxymethyl]butyl)guanine ([$^{18}$F] FHBG); 2'-deoxy-2'-[$^{18}$F]-fluoro-1-beta-D-arabinofuranosyl-5-iodouracil ([$^{18}$F] FEAU), 2'-deoxy-2'-[$^{18}$F]-fluoro-5-methyl-1-β.-L-arabiriofuranosyluracil ([$^{18}$F] FMAU), 1-(2'-deoxy-2'-fluoro-beta-D-arabinofuranosyl)-5-[$^{18}$F] iodouracil ([$^{15}$F] FIAU), 2'-deoxy-2'-[$^{18}$F]-fluoro-1-beta-D-arabinofuranosyl-5-iodouracil ([$^{18}$F] FIAC, see, for example, Chan et al., Nuclear Medicine and Biology 38 (2011) 987-995; and Cal et al., Nuclear Medicine and Biology 38 (2011) 659-666); various alkylated pyrimidine derivatives such as a C-6 alkylated pyrimidine derivative described by Muller et al. (Nuclear Medicine and Biology, 2011, in press); and others.

Other exemplary reporter molecules may retain or cause retention of a detectably labeled complement by any of a variety of mechanisms. For example, the reporter molecule may bind to the complement very strongly (e.g. irreversibly) and thus increase the local concentration of the complement within cancer cells; or the reporter molecule may modify the complement in a manner that makes egress of the complement from the cell difficult, or at least slow enough to result in a net detectable accumulation of complement within the cell; or the reporter may render the complement suitable for participation in one or more reactions which "trap" or secure the complement, or a modified form thereof that still includes the detectable label, within the cell, as is the case with the TK. example presented above.

One example of such a system would be an enzyme-substrate complex, in which the reporter is usually the enzyme and the complement is usually the substrate, although this need not always be the case: the reporter may encode a polypeptide or peptide that is a substrate for an enzyme that functions as the "complement". In some embodiments, the substrate is labeled with a detectable label (e.g. a radio-, fluorescent-, phosphorescent-, colorimetric-, light emitting-, or other label) and accumulates within cancer cells due to, for example, an irreversible binding reaction with the enzyme (i.e. it is a suicide substrate), or because it is released from the enzyme at a rate that is slow enough to result in a detectable accumulation within cancer cells, or the reaction with the enzyme causes a change in the properties of the substrate so that it cannot readily leave the cell, or leaves the cell very slowly (e.g. due to an increase in size, or a change in charge, hydrophobicity or hydrophilicity, etc.); or because, as a result of interaction or association with the enzyme, the substrate is modified and then engages in subsequent reactions which cause it (together with its detectable tag or label) to be retained in the cells, etc.

Other proteins that may function as reporter molecules in the practice of the invention are transporter molecules which are located on the cell surface or which are transmembrane proteins, e.g. ion pumps which transport various ions across cells membranes and into cells. An exemplary ion pup is the sodium-iodide symporter (NIS) also known as solute carrier family 5, member 5 (SLC5A5). In nature, this ion pump actively transports iodide (I−) across e.g. the basolateral membrane into thyroid epithelial cells. Recombinant forms of the transporter encoded by sequences of the constructs described herein may be selectively transcribed in cancer cells, and transport radiolabeled iodine into the cancer cells. Other examples of this family of transporters that may be used in the practice of the invention include but are not limited to norepinephrine transporter (NET); dopamine receptor; various estrogen receptor systems), ephrin proteins such as membrane-anchored ephrin-A (EFNA) and the transmembrane protein ephrin-B (EFNB); epidermal growth factor receptors (EGFRs); insulin-like growth factor receptors (e.g. IGF-1, IGF-2), etc.); transforming growth factor (TGF) receptors such as TGFα; etc. In these cases, the protein or a functional modified form thereof is expressed by the vector of the invention and the ligand molecule is administered to the patient. Usually, the ligand is labeled with a detectable label as described herein, or becomes detectable upon association or interaction with the transporter. In some embodiments, detection may require the association of a third entity with the ligand, e.g. a metal ion. The ligand may also be a protein, polypeptide or peptide.

In addition, antibodies may be utilized in the practice of the invention. For example, the vectors of the invention may be designed to express proteins, polypeptides, or peptides which are antigens or which comprise antigenic epitopes for which specific antibodies have been or can be produced. Exemplary antigens include but are not limited to tumor specific proteins that have an abnormal structure due to mutation (protooncogenes, tumor suppressors, the abnormal products of ras and p53 genes, etc.); various tumor-associated antigens such as proteins that are normally produced in very low quantities but whose production is dramatically increased in tumor cells (e.g. the enzyme tyrosinase, which is elevated in melanoma cells); various oncofetal antigens (e.g. alphafetoprotein (AFP) and carcinoembryonic antigen (CEA); abnormal proteins produced by cells infected with oncoviruses, e.g. EBV and HPV; various cell surface glycolipids and glycoproteins which have abnormal structures in tumor cells; etc. The antibodies, which may be monoclonal or polyclonal, are labeled with a detectable label and are administered to the patient after or together with the vector. The antibodies encounter and react with the expressed antigens or epitopes, which are produced only (or at least predominantly) in cancer cells, thereby labeling the cancer cells. Conversely, the antibody may be produced by the vector of the invention, and a labeled antigen may be administered to the patient. In this embodiment, an antibody or a fragment thereof, e.g. a Fab (fragment, antigen binding) segment, or others that are known to those of skill in the art, are employed. In this embodiment, the antigen or a substance containing antigens or epitopes for which the antibody is specific is labeled and administered to the subject being imaged.

Other examples of such systems include various ligand binding systems such as reporter proteins/polypeptides that bind ligands which can be imaged, examples of which include but are not limited to: proteins (e.g. metalloenzymes) that bind or chelate metals with a detectable signal; ferritin-based iron storage proteins such as that which is described by Iordanova and Ahrnes (Neuroimage. 2012 Jan. 16; 59 (2):1004-12.); and others. Such systems of reporter and complement may be used in the practice of the invention, provided that the reporter or the complement can be transcribed under control of a cancer promoter, and that the other binding partner is detectable or can be detectably labeled, is administrable to a subject, and is capable of diffusion into cancer cells. Those of skill in the art will recognize that some such systems are suitable for use e.g. in human subjects, while other are not due to, for example, toxicity. However, systems in the latter category may be well-suited for use in laboratory settings.

In yet other aspects, the cancer-specific or cancer-selective promoters in the vectors of the invention drive expression of a secreted protein that is not normally found in the circulation. In this embodiment, the presence of the protein may be detected by standard (even commercially available) methods with high sensitivity in serum or urine. In other words, the cancer cells that are detected are detected in a body fluid.

In yet other aspects, the cancer-specific or cancer-selective promoters in the vectors of the invention drive transcription of a protein or antigen to be expressed on the cell surface, which can then be tagged with a suitable detectable antibody or other affinity reagent. Candidate proteins for secretion and cell surface expression include but are not limited to: β-subunit of human chorionic gonadotropin (β hCG); human α-fetoprotein (AFP), and streptavidin (SA).

β hCG is expressed in pregnant women and promotes the maintenance of the corpus luteum during the beginning of pregnancy. The level of β hCG in non-pregnant normal women and men is 0-5 mIU/mL. KG is secreted into the serum and urine and β hCG has been used for pregnancy test since the β-subunit of hCG is shared with other hormones. Urine β hCG can be easily detected by a chromatographic immunoassay (i.e. pregnancy test strip, detection threshold is 20-100 mIU/mL) at home-physician's office- and laboratory-based settings. The serum level can be measured by chemiluminescent or fluorescent immunoassays using 2-4 mL of venous blood for more quantitative detection. β hCG has been shown to secreted into the media when it was expressed in monkey cells. Human AFP is an oncofetal antigen that is expressed only during fetal development and in adults with certain types of cancers. AFP in adults can be found in hepatocellular carcinoma, testicular tumors and metastatic liver cancer. AFP can be detected in serum, plasma, or whole blood by chromatographic immunoassay and by enzyme immunoassay for the quantitative measurement.

Streptavidin (SA) can also be used as a cell surface target in the practice of the invention. The unusually high affinity of SA with biotin provides very efficient and powerful target for imaging and therapy. To bring SA to the plasma membrane of the cancer cells, SA can be fused to glycosylphosphatidylinositol (GPI)-anchored signal of human CD14. GPI-anchoring of SA will be suitable for therapeutic applications since GPI-anchor proteins can be endocytosed to the recycling endosomes. Once expressed on the cell surface, SA can then be bound by avidin conjugates that contain a toxic or radiotoxic warhead. Toxic proteins and venoms such as ricin, abrin, *Pseudomonas* exotoxin (PE, such as PE37, PE38, and PE40), diphtheria toxin (DT), saporin, restrictocin, cholera toxin, gelonin, Shigella toxin, and pokeweed antiviral protein, *Bordetella pertussis* adenylate cyclase toxin, or modified toxins thereof, or other toxic agents that directly or indirectly inhibit cell growth or kill cells may be linked to avidin; as could toxic low molecular weight species, such as doxorubicin or taxol or radionuclides such as $^{125}$I, $^{131}$I, $^{111}$In, $^{177}$Lu, $^{211}$At, $^{225}$Ac, $^{213}$Bi and $^{90}$Y; antiangiogenic agents such as thalidomide, angiostatin, anti-sense molecules, COX-2 inhibitors, integrin antagonists, endostatin, thrombospondin-1, and interferon alpha, vitaxin, celecoxib, rofecoxib; as well as chemotherapeutic agents such as: pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers; caspase activators; and chromatin disruptors, especially those which can be conjugated to nanoparticles The detectable components of the system (usually a complement or substrate) may be labeled with any of a variety of detectable labels, examples of which are described above. In addition, especially useful detectable labels are those which are highly sensitive and can be detected non-invasively, such as the isotopes $^{124}$I, $^{123}$I, $^{99m}$Tc, $^{18}$F, $^{86}$Y, $^{11}$C, $^{125}$I, $^{64}$Cu, $^{67}$Ga, $^{68}$Ga, $^{201}$Tl, $^{76}$Br, $^{75}$Br, $^{111}$In, $^{82}$Rb, $^{13}$N, and others.

Those of skill in the art will recognize that many different detection techniques exist which may be employed in the practice of the present invention, and that the selection of one particular technique over another generally depends on the type of signal that is produced and also the medium in which the signal is being detected, e.g. in the human body, in a laboratory animal, in cell or tissue culture, ex vivo, etc. For example, bioluminescence imaging (BLI); fluorescence imaging; magnetic resonance imaging [MRI, e.g. using lysine rich protein (LRp) as described by Gilad et al., Nature Biotechnology, 25, 2 (2007); or creatine kinase, tyrosinase, β-galactosidase, iron-based reporter genes such as transferring, ferritin, and MagA; low-density lipoprotein receptor-related protein (LRP; polypeptides such as poly-L-lysine, poly-L-arginine and poly-L-threonine; and others as described, e.g. by Gilad et al., J. Nucl. Med. 2008; 49(12): 1905-1908); computed tomography (CT); positron emission tomography (PET); single-photon emission computed tomography (SPECT); boron neutron capture; for metals: synchrotron X-ray fluorescence (SXRF) microscopy, secondary ion mass spectrometry (SIMS), and laser ablation inductively coupled plasma mass spectrometry (LA-ICP-MS) for imaging metals; photothermal imaging (using for example, magneto-plasmonic nanoparticles, etc.

For aspects of the invention that encompass both treatment and imaging, the administration protocols may be any which serve the best interest of the patient. For example, initially, an imaging vector alone may be administered in order to determine whether or not the subject does have cancer, or to identify the locations of cancer cells in a patient that has already been diagnosed with cancer. If cancer is indeed indicated, then compositions with therapeutic vectors are administered as needed to treat the disease. Usually a plurality of administrations is required as discussed above, and one or more, and sometimes all, include at least one imaging vector together with a least one therapeutic vector; or optionally, a single vector with both capabilities. The ability to alternate between therapy and imaging, or to concomitantly carry out both, is a distinct boon for the field of cancer treatment. This methodology allows a medical professional to monitor the progress of treatment in a tightly controlled manner, and to adjust and/or modify the therapy as necessary for the benefit of the patient. For example, administration of a therapeutic and an imaging vector may be alternated; or, during early stages of treatment, initially an imaging vector may be administered, followed by therapy and imaging vectors together until the tumors are no longer visible, followed by imaging vector alone for a period of time deemed necessary to rule out or detect recurrence or latent disease.

Monitoring may involve a step of imaging, followed by a step of administering an agent (or administering a combined theranostic followed by immediate imaging), and then repeated steps of re-imaging (imaging again, e.g. a first or pre- or early-therapeutic imaging step), followed by subsequent additional imaging to determine the effect of the therapy (e.g. second, third, fourth, etc. imaging or re-imaging steps) to monitor the size and location of tumors and cancer cells after therapies have been provided to the patient. A comparison of the first or early images to those obtained later, e.g. after therapy, is used to draw a conclusion regarding whether or not the therapy is having a desired effect (e.g. killing or eliminating cancer cells or slowing tumor growth, and/or preventing or eliminating or slowing metastasis, etc.). If a desired outcome is observed, then the therapy may be continued as originally planned, with periodic re-imaging to check further progress. However, is a desired outcome is not observed (e.g. number or amount of cancer cells the same or increased, tumor volume the same or increased), then the therapeutic regimen may be altered, for example, by increasing a dose or frequency of administration of one or more therapeutic agents. Those of skill in the art will recognize that even though the goal of therapy is to eliminate or "cure" the cancer, less desirable outcomes may still be beneficial to the patient e.g. by slowing the progress of the disease, extending life expectancy, etc.

The agents of the invention may also be used for long-term monitoring and/or monitoring and treatment of cancer, as required for the benefit of the patient.

Compositions

The present invention provides compositions, which comprise one or more vectors or constructs as described herein and a pharmacologically suitable (physiologically acceptable) carrier. The compositions may be for systemic administration. The preparation of such compositions is known to those of skill in the art. Typically, they are prepared either as liquid solutions or suspensions, or as solid forms suitable for solution in, or suspension in, liquids prior to administration. The preparation may also be emulsified. The active ingredients may be mixed with excipients, which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any of one or more ingredients known in the art to provide the composition in a form suitable for administration. The final amount of vector in the formulations may vary. However, in general, the amount in the formulations will be from about 1-99%.

Types of Cancer that can be Treated and/or Imaged

The constructs and methods of the invention are not specific for any one type of cancer. By "cancer" we mean malignant neoplasms in which cells divide and grow uncontrollably, forming malignant tumors, and invade nearby parts of the body. Cancer may also spread or metastasize to more distant parts of the body through the lymphatic system or bloodstream. The constructs and methods of the invention may be employed to image, diagnose, treat, monitor, etc. any type of cancer, tumor, neoplastic or tumor cells including but not limited to: osteosarcoma, ovarian carcinoma, breast carcinoma, melanoma, hepatocarcinoma, lung cancer, brain cancer, colorectal cancer, hematopoietic cell, prostate cancer, cervical carcinoma, endometrial carcinoma, vulvar carcinoma, retinoblastoma, esophageal carcinoma, bladder cancer, neuroblastoma, renal cancer, gastric cancer, pancreatic cancer, gestational trophoblastic disease, uterine sarcoma, vaginal carcinoma, and others.

In addition, the invention may also be applied to imaging and therapy of benign tumors, which are generally recognized as not invading nearby tissue or metastasizing, for example, moles, uterine fibroids, etc.

Transgenic Animals

This disclosure also provides transgenic non-human eukaryotic animals or other eukaryotic organisms (e.g. insects) whose germ cells and somatic cells contain at least one gene of interest under operational control of the tCCN1 promoter, and offspring and cells thereof (whether present in the animal or excised (removed) from the animal). In one aspect, the transgenic animal is a mouse, although transgenic animals of other species are also encompassed, e.g. rats, guinea pigs, pigs, hamsters, rabbits, primates, fish, drosophila, etc.

In one aspect, the at least one gene of interest that is under operational control of the tCCN1 promoter is a reporter gene as described herein, such as a luciferase gene.

Those of skill in the art are familiar with various methods of generating transgenic non-human animals. See, for example, U.S. Pat. Nos. 6,018,097 and 6,262,335 and US patent applications 20060179501 and 2002003791, the complete contents of each of which are hereby incorporated by reference in entirety. Techniques for creating transgenic non-human animals include but are not limited to e.g. by microinjection, using retroviral vectors, via embryonic stem cell transfer, etc. (see, for example, U.S. Pat. Nos. 6,080,912 and 5,175,384, the complete contents of which are hereby incorporated by reference in entirety).

In an exemplary procedure, generation and identification of CCN1-luc2 (i.e. tCCN1-Prom-luc) transgenic mice was accomplished as follows: To generate CCN1-luc2 (tCCN1-luc2) transgenic mice, a 4.1-kb AccI fragment was excised from the CCN1-luc2 construct (pGL4.tCCN1-Prom-β-globin (intron 2)-luc2) and microinjected into the male pronucleus of fertilized single-cell mouse embryos obtained from mating CB6F1 (C57BL/6×Balb/C) males and females. The injected embryos were then reimplanted into the oviducts of pseudopregnant CD-1 female mice. Offspring were screened for the CCN1-luc2 transgene by PCR analysis of genomic tail DNA using a β-globin intron 2 sense primer (5'-CCCTCTGCTAACCATGTTCATGC-3', SEQ ID NO: 4) and a luc2 antisense primer (5'-TCTTGCTCACGAATAC-GACGGTG-3', SEQ ID NO: 5), with a PCR product of 544 bp detected in transgenic mice.

In some aspects, the transgenic animals are single transgenic animals having a single transgene. Alternatively, the animals may be doubly, triply, etc. transgenic e.g. by insertion of a second, third, etc. expressible transgene, or by cross breeding the animals with another transgenic animal. Generally, the transgenic traits are stably maintained in the animal from generation to generation, e.g. offspring also possess the traits. The genes of interest under control of e.g. the tCCN1 promoter may be integrated into the animal's chromosome or may remain as generationally transmissible extra-chromosomal elements. Alternatively, the genes may be transiently expressed in the animal.

In one aspect, the transgenic animal is doubly transgenic for a reporter gene and a gene that causes the development of cancer. Such transgenic animals that contain an expressible reporter gene under control of the tCCN1 cancer selective promoter may be used for a variety of applications. For example, the progression of cancer may be studied using the mice by imaging at various stages of cancer progression and/or under various conditions, e.g. after exposure or administration of various treatment modalities. The animals may be used to screen candidate therapeutics by administering a candidate therapeutic or combination of therapeutics, and monitoring the progression of the cancer in comparison to control animals who do not receive the treatment, and/or who receive other treatments.

Transgenic animals having only a reporter gene under control of the tCCN1 promoter may be used to assess the cancer-causing effects of various substances or conditions to which they are exposed, e.g. various suspected carcinogens, various environmental conditions, dietary influences, lifestyle influences (e.g. exercise, stress, etc.); and the like.

For all such screening and testing procedures, typically the results are expressed in suitable measured units, e.g. time until tumor development, tumor volume, metastasis occurrence, tumor shrinkage, etc. and the results are compared to that of one or more suitable control values. The comparison allows a skilled practitioner to conclude whether or not the experimental variable (e.g. the candidate therapeutic, the possible carcinogen, etc.) has exerted an effect that differs from that seen in suitable, matched control animals. For example, a decrease in the incidence of cancer development, or a decrease in metastasis, or a decrease in tumor volume, compared to an untreated control, would support a conclusion that a candidate therapeutic should be selected as efficacious in preventing or treating cancer, as appropriate. And the development of cancer in response to exposure to a potential carcinogen would indicate that the substance or condition is indeed carcinogenic, while the absence of cancer would warrant the opposite conclusion.

The following examples are provided in order to illustrate several examples of the practice of the invention, but should not be construed as limiting the invention in any way.

EXAMPLES

A truncated tCCN1 promoter (~830-kb fragment; attached sequence with the binding elements and transcription factors) was cloned by amplifying the genomic DNA isolated from IM-PHFA (telomerase immortalized primary human fetal astrocytes) using primers 5'TCCAAAAACAAACAAGTACAACAT'3 (SN; SEQ ID NO: 2) and 5'GGCGCCCCGGAGCCCGCCTTTTATA'3 (AS, SEQ ID NO: 3). The (CCN1 promoter construct was cloned into the luciferase reporter vector pGL3 basic (Promega, Madison, Wis., USA) to produce the pGL3.CCN1-luc (pCCN1-luc i.e., ptCCN1-luc) construct. This construct was used for subsequent experiments.

Materials and Methods:
Cell Transfection and Luciferase Assay:

Prostate cancer cells were plated at seeding density of 30,000 cells/well in quadruplicate in 24-well cell culture plate. After 24 h, cells were transfected with either pGL3.PEG-luc or pGL3.CCN1-hie using Fugene® HD transfection reagent (Promega, Madison, Wis., USA). For normalization, the indicated plasmids were co-transfected with pRL-TK at the ratio of 20:1. Cells were lysed after 48 h of post transfection and luminescence was studied using Dual-luciferase Reporter® Assay system (Promega) with luminometer.

Figure 2B:
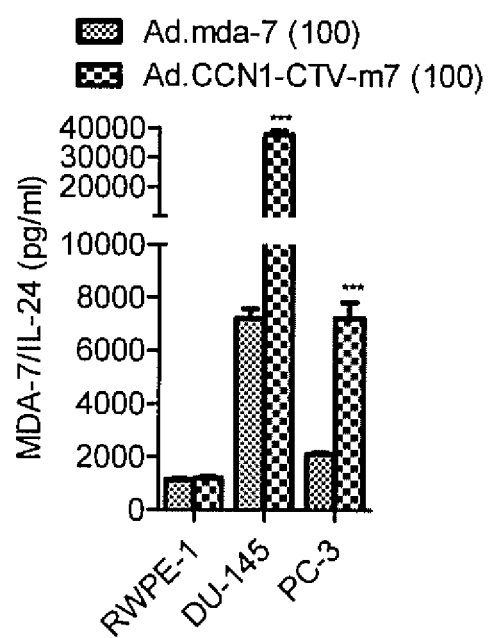

Construction of Ad.CCN1-E1A-mda-7 (Ad.CCN1-CTV-m7):

To construct Ad.CCN1-E1A-mda-7, AdenoQuick cloning system (OD260, Inc., Boise, Id., USA) was employed. This system utilizes two shuttle vectors (pE1.2 and pE3.1-CMV) in which the transgenes must be inserted before being transferred into a large adenoviral plasmid (pAd) (FIG. 2). The E1A region has been deleted from pAd leaving the E1B region intact. The expression cassette in which the tCCN1-Prom drives early region E1A (CCN1-E1A) of Ad was inserted into the multiple cloning site (MCS) of pE1.2 (i.e. pE1.2-CCN1-E1A). The other expression cassette, in which CMV-Prom drives the expression of mda-7/IL-24, was inserted into the MCS of pE3.1 (i.e. pE3.1-CMV-mda-7). In both shuttle plasmids the MCS are flanked by two sets of restriction sites. pE1.2-CCN1-E1A and pE3.1-CMV-mda-7 were digested with Restriction enzymes (R.E) with AlwNI, BstAPI, DraIII or PflMI. pAd was digested with SfiI to generate sticky ends with deleted E1A (ΔE1) and E3 (ΔE3). The sticky ends of ΔE1 region are incompatible with each other and with those present in the ΔE3 region but are compatible with those generated by digesting plasmid pE1.2-CCN1-E1A with AlwNI, DraIII or PflMI. The sticky ends of ΔE3 region are incompatible with each other and with those present in the ΔE1 region but are compatible with those generated by digesting plasmid pE3.1-CMV-mda-7 with AlwNI, BstAPI, DraIII or PflMI. Upon ligation of the expression cassettes at the respective specific sites, the ligated product was transformed into E. coli to select the clones pAd.CCN1-E1A-CMV-mda-7 with ampicillin (amp$^R$ provided by pAd) and kanamycin (Kan$^R$ provided by shuttle vector). The resultant plasmid pAd.CCN1-E1A-CMV-mda-7 was digested with PacI to release viral ITRs and was transfected into HEK-293 cells to rescue the conditional replication-competent Ad (CRCA); Ad.CCN1-E1A-mda-7), Similar strategies were used to construct Ad.mda-7 and Ad.CCN1-E1A constructs. The constructs were purified using CsCl gradient, titrated both by OD260-SDS (vp/ml) (Optical absorbance at 260 nm of lysed Ad using 0.1% Sodium dodecyl-sulphate solution) method and TCID50 (median or 50% tissue culture infective dose) or plaque forming methods (pfu/ml).

Ads Infection and Cell Proliferation Assay:

Prostate cancer cells were infected with Ad.vec or Ad.mda-7 or Ad.CCN1-E1A or Ad.CCN1-E1A-mda-7 (Ad.CCN1-CTV-m7) for 3-h in medium without Fetal bovine serum (FBS) followed by addition of medium with 10% FBS. The treated cells analyzed for cell proliferation by MTT dye reduction assay.

Developing In Vivo Metastatic Model:

$3 \times 10^6$ PC-3-ML cells were injected via intra-cardiac route in 2-3 month old SCID mice. Mice were imaged after 4-5 weeks to observe micrometastases.

In Vivo Transfection in Prostate Cancer Metastases Model:

Transfection in vivo was done using jet-PEI DNA transfection kit (Polyplus) as par as manufacturer's instructions. Each animal received a tail vein injection of 60 μg, DNA of pGL3.CCN1-luc2 after forming jet-PEI/nucleic acid mixes. Mice were imaged after 48 h post injection using IVIS Spectrum after 10 min post i.p injection of D-luciferin (150 mg/kg body wt).

Bioluminescence Imaging (BLI):

Image acquisition was done in 2D bioluminescence imaging (BLI) and 3D Diffused Luminescence Imaging Tomography (DLIT) mode using IVIS spectrum and analyzed by Living Image 4.3.1. 3D DLIT image was further reconstructed with digital anatomical structure of the mice after aligning and fitting the surface of the mice to obtain reconstructed 3D-DLIT to know the precise location and strength of BLI signal.

Monitoring Metastases Using BLI:

Mice were imaged over time and image analysis was done using Living Image 4.3.1 and GraphPad Prism 5.0.

Cloning of the CCN1-luc2 Transgene Construct:

To generate the CCN1-luc2 transgene construct, an 831-bp fragment of the human truncated tCCN1 promoter was inserted into the multiple cloning site of the pGL4.10[luc2] vector (Promega). pGL4.10[/luc2] encodes a synthetic firefly luciferase gene from Photinus pyralis (luc2), and contains the SV40 late polyadenylation signal downstream of luc2 as well as a synthetic polyadenylation signal upstream of the multiple cloning sites to reduce background transcription. For efficient transgene expression a 644-bp region of the rabbit β-globin gene containing β-globin intron 2 was also inserted between the tCCN1 promoter and the luc2 gene.

Generation and Identification of tCCN1-luc2 Transgenic Mice:

To generate CCN1-luc2 i.e. tCCN1-luc2 transgenic mice, a 4.1-kb AccI fragment was excised from the CCN1-luc2 (tCCN1-luc2) construct and microinjected into the male pronucleus of fertilized single-cell mouse embryos obtained from mating CB6F1 (C57BL/6×Balb/C) males and females. The injected embryos were then reimplanted into the oviducts of pseudopregnant CD-1 female mice. Offspring were screened for the CCN1-luc2 (tCCN1-luc2) transgene by PCR analysis of genomic tail DNA using a (I-globin intron 2 sense primer (5'-CCCTCTGCTAACCATGTTCATGC-3'. SEQ ID NO: 4) and a luc2 antisense primer (5'-TCTTGCT-CACGAATACGACGGTG-3', SEQ ID NO: 5), with a PCR product of 544 bp detected in transgenic mice.

Generation of Compound Transgenic tCCN1-luc-MMTV-PyMT (tCCN1-luc-MMTV-PyMT) Mice:

Potential founders carrying the CCN1-luc2 (tCCN1-luc2) transgene have been generated and positivity for the transgene has been confirmed by screening with PCR. Compound transgenic mice were developed with tCCN1-luc-MMTV-PyMT by mating transgenic MMTV-PyMT males with transgenic females from tCCN1-luc2 lines, Compound transgenic mice were confirmed by PCR. CCN1-luc-MMTV-PyMT (tCCN1-luc-MMTV-PyMT) compound transgenic breast cancer mice were imaged by Xenogen IVIS 200 optical imager and analyzed using Living Image software after i.p. administration of D-luciferin (150 mg/kg body weight).

Example 1. Comparison of the Ability of PEG and tCCN1 Promoters to Drive Expression of Luciferase in Normal Prostate and Prostate Cancer Cells Cells from prostate cancer cells lines DU-145, PC-3, ARCaP, ARCaP-E, ARCaP-M and normal human prostate epithelial cell lines RWPE-1 and P69 were infected with the pGL3-luc reporter vector driven by PEG-Prom (pPEG-luc) or by tCCN1-Prom (pCCN1-luc). pRL-TK (Renilla luciferase) was co-transfected for the normalization of luciferase activity. The results are presented in FIG. 1A. src-, raf-, ras- and HPV-transformed CREF cells were treated with p-CCN1-luc and/or TPA (200 ng/ml). The results are presented in FIG. 1B.

Conclusions:
1. tCCN1-Prom is more active than the PEG-Prom in prostate cancer cells as compared to normal counterparts RWPE-1 and P69, suggesting cancer-selective activity in prostate cancer cells.
2. tCCN1-Prom activity is elevated as a function of transformation of CREF cells by diverse acting oncogenes.
3. TPA and cyclic adenosine mono-phosphate (AMP) increased the expression of the tCCN1-Prom, indicating the involvement of protein kinase C (PKC) and cyclic AMP-response element (CRE) binding protein (CREB) in regulating the expression of CCN1 in various cell lines. Activity of the tCCN1-Prom is elevated in transformed, but not in normal CREF cells.
4. tCCN1-Prom also displays elevated expression in additional human cancers vs. normal immortal or primary normal counterparts, including breast, brain (including Glioblastoma multiforme, GBM) and melanoma (data not shown).
5. tCCN1-Prom expression positively correlates with transformation and tumorigenesis metastasis. Therefore, tCCN1-Prom displays cancer-specific activity and can be used to drive expression of genes of interest in a tumor-selective manner, e.g. in conditionally-replication competent oncolytic viruses.

Example 2. Construction and Testing of a Conditionally-Replication Competent Oncolytic Adenovirus Conditionally-replication competent oncolytic adenovirus (Ad.CCN1-E1A-mda-7), a so-called "Cancer Terminator Virus" or "CTV" was constructed (see FIG. 2A). In Ad.CCN1-E1A-mda-7, the tCCN1-Prom regulates the expression of E1A and E1B genes and was placed in the deleted region of the E1A and E1B regions of the plasmid pAd. Cytomegalovirus promoter (CMV-Prom) regulates the expression of the anti-cancer cytokine mda-7/IL-24 and these elements were inserted in the deleted region of E3 of pAd. This viral construct does not harm normal cells but induces oncolysis by Adenoviral replication and diverse tumor-suppressor effects of the expressed transgene mda-7/IL-24.

MDA-7/IL-24 protein expression in conditioned medium of prostate cancer cells and normal human immortalized prostate epithelial cells RWPE-1 after infection with Ad.mda-7 (100 vp/cell) and Ad.CCN1-CTV-m7 (100 vp/cell) as measured by human IL-24 ELISA kit. The results are presented in FIG. 2B.

Conclusions:
1. Ad.CCN1-E1A-CMV-mda-7 (Ad.CCN1-CTV-m7) was successfully constructed. In this CTV, replication is controlled by tCCN1-Prom with robust production of MDA-7/IL-24 under the regulation of the CMV-Prom. Its predicted activity was confirmed by ELISA.
2. The oncolytic properties, including both direct and 'bystander' anti-tumor effects of mda-7/IL-24, as expressed from this exemplary viral construct are active in primary tumors as well as metastatic tumors.

Example 3. Cancer Specific Oncolysis and Cell Death Reflected by a Decrease in Cell Proliferation Following Infection with Ad.CCN1-CTV-m7

Figure 3:
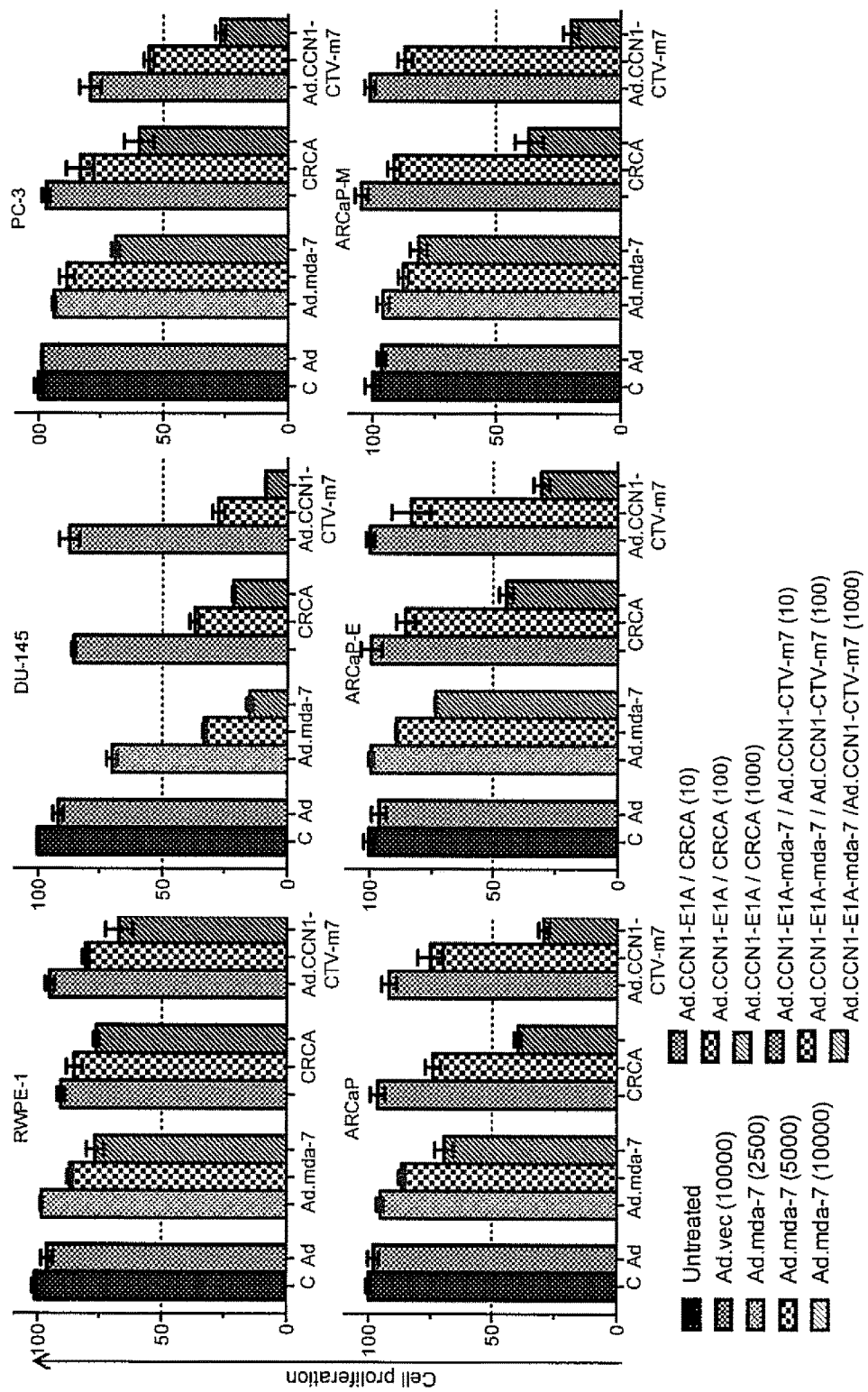
FIG. 3. Cancer specific oncolysis and cell death reflected by a decrease in cell proliferation following infection with Ad.CCN1-CTV-m7. MTT assays of prostate cancer and normal immortal RWPE-1 cells treated with Ad.vec, Ad.mda-7, Ad.CCN1-E1A (CRCA) and Ad.CCN1-E1A-coda-7 (Ad.CCN1-CTV-m7) at indicated vp/cell for 3 days.

Prostate cancer and normal immortal RWPE-1 cells treated with Ad.vec, Ad.mda-7, Ad.CCN1-E1A (CRCA) and Ad.CCN1-E1A-mda-7 (Ad.CCN1-CTV-m7) at indicated vp/cell for 3 days as described in Materials and Methods. MTT assays were conducted and the results are presented in FIG. 3.

Conclusions:
1. The CTVs (Ad.CCN1-E1A-mda-7 or Ad.CCN1-CTV-m7) more efficiently kill PC cells than a replication incompetent Ad.mda-7,
2, Both Ad.CCN1-E1A (CRCA) (a conditionally cancer-selective replicating virus) and Ad.CCN1-E1A-mda-7 (Ad.CCN1-CTV-m7) induce killing in PC cells in a dose-dependent manner.
3. In vitro studies suggest that the cells are preferentially killed by the oncolytic properties of the CRCAs, rather than by the 'bystander' effects produced by mda-7/IL-24.

Figure 4:
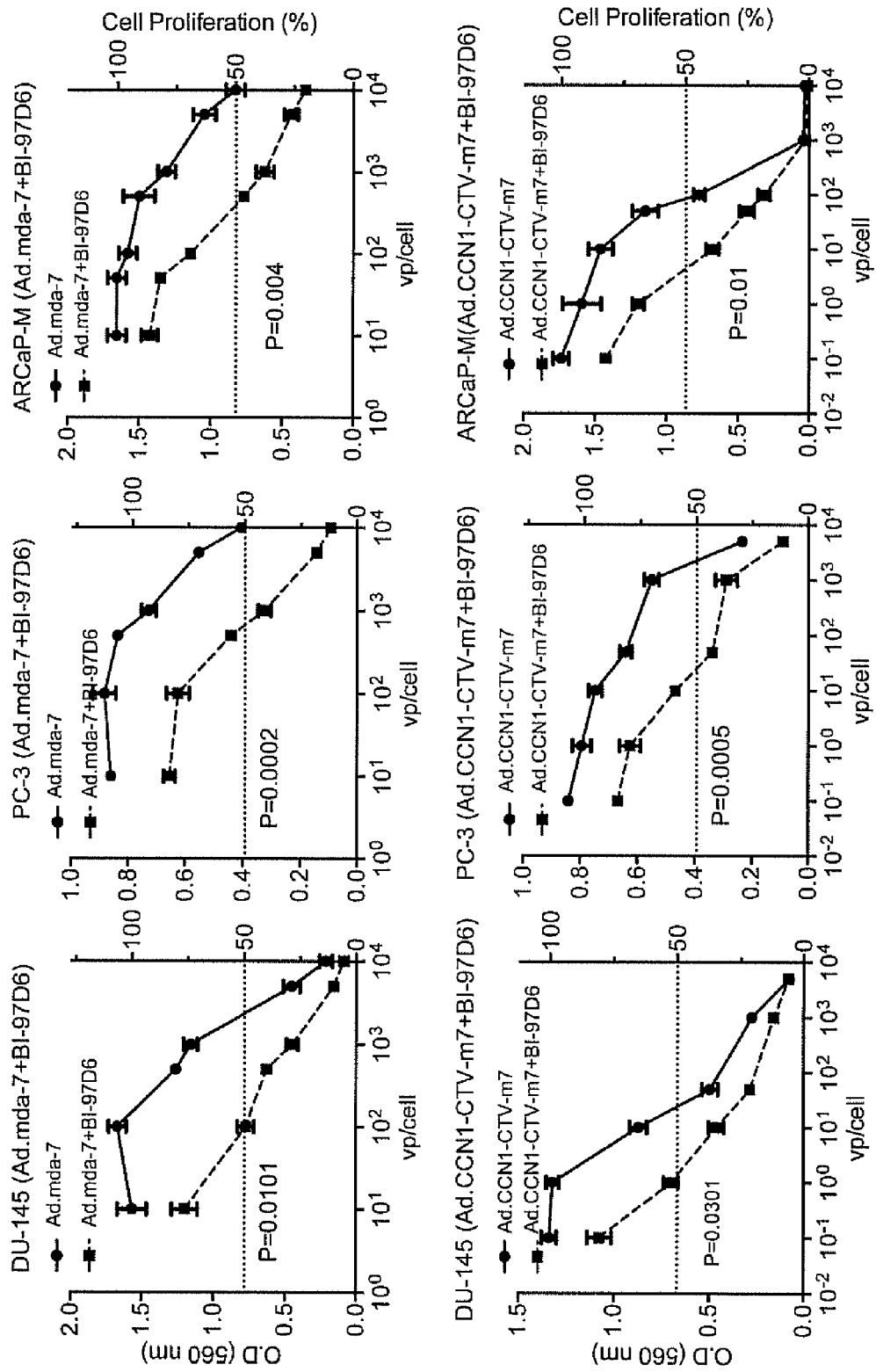
FIG. 4. BI-97D6 potentiates mda-7/IL-24-induced inhibition in PC cell growth in vitro. DU-145, PC-3 and ARCaP-M cells were infected with the indicated M.O.I. of Ads followed by treatment with a sub-lethal dose of 250 nM BI-97D6. Cell growth was assessed after 3 days using MTT dye reduction assays.

Example 4. BI-97D6 Potentiates mda-7/IL-24-Induced Inhibition of PC Cell Growth in Vitro DU-145, PC-3 and ARCaP-M cells were infected with the multiplicity of infection (M.O.I.) of adenoviral vectors indicated in the legend of FIG. 4. Infection was followed either by treatment with a sub-lethal dose (250 nm) of BI-97D6. BI-97D6 is a broad spectrum BH3 mimetic that induces apoptosis (Wei et al, J Med Chem. 2010). Cell growth was assessed after 3 days using tetrazolium dye MTT reduction assays. The results are presented in FIG. 4, Conclusions:
1. Ectopic expression of mda-7/IL-24 in PC cells leads to a dramatic decrease in anti-apoptotic Bcl-2 family member proteins, especially Mcl-1 (Dash. et al., 2011).
2. Thus, BI-13 mimetics such as BI-97D6 have inhibitory effects against Mcl-1 and can be used in combination with mda-7/IL-24 to sensitize PC cells to mda-7-induced apoptosis.
3. PC cells were treated with 250 nM (suboptimal dose) of BI-97D6 in combination with a replication incompetent Ad.mda-7 or a conditionally replication competent Ad.CCN1-E1A-mda-7 (Ad.CCN1-CTV-m7).
4. There was a significant decrease in cell proliferation in DU-145, PC-3 and ARCaP-M cells treated with Ad.mda-7 plus BI-97D6 as compared to Ad.mda-7 treatment alone.
5. As compared to non-replicating Ad.mda-7, conditionally replicating Ad.CCN1-E1A-mda-7 (Ad.CCN1-CTV-m7) was superior in inhibiting cell proliferation.
6. The $IC_{50}$ of Ad.CCN1-E1A-mda-7 (Ad.CCN1-CTV-m7)-treated PC cells were at least 100-fold less as compared to non-replicating Ad.mda-7.
7. These results have significant clinical value since administering an adequate titer of Ad.CCN1-E1A-mda-7 (Ad.CCN1-CTV-m7) can easily be achieved based on its cancer-specific replication at the tumor site, which is not achievable with a non-replicating Ad.mda-7. Moreover, combining Ad.CCN1-E1A-mda-7 (Ad.CCN1-CTV-m7) with BI-97D6 enhanced the decrease in cell growth as compared to cells treated solely with Ad.CCN1-E1A-mda-7 (Ad.CCN1-CTV-m7).

Example 5

Figure 5:
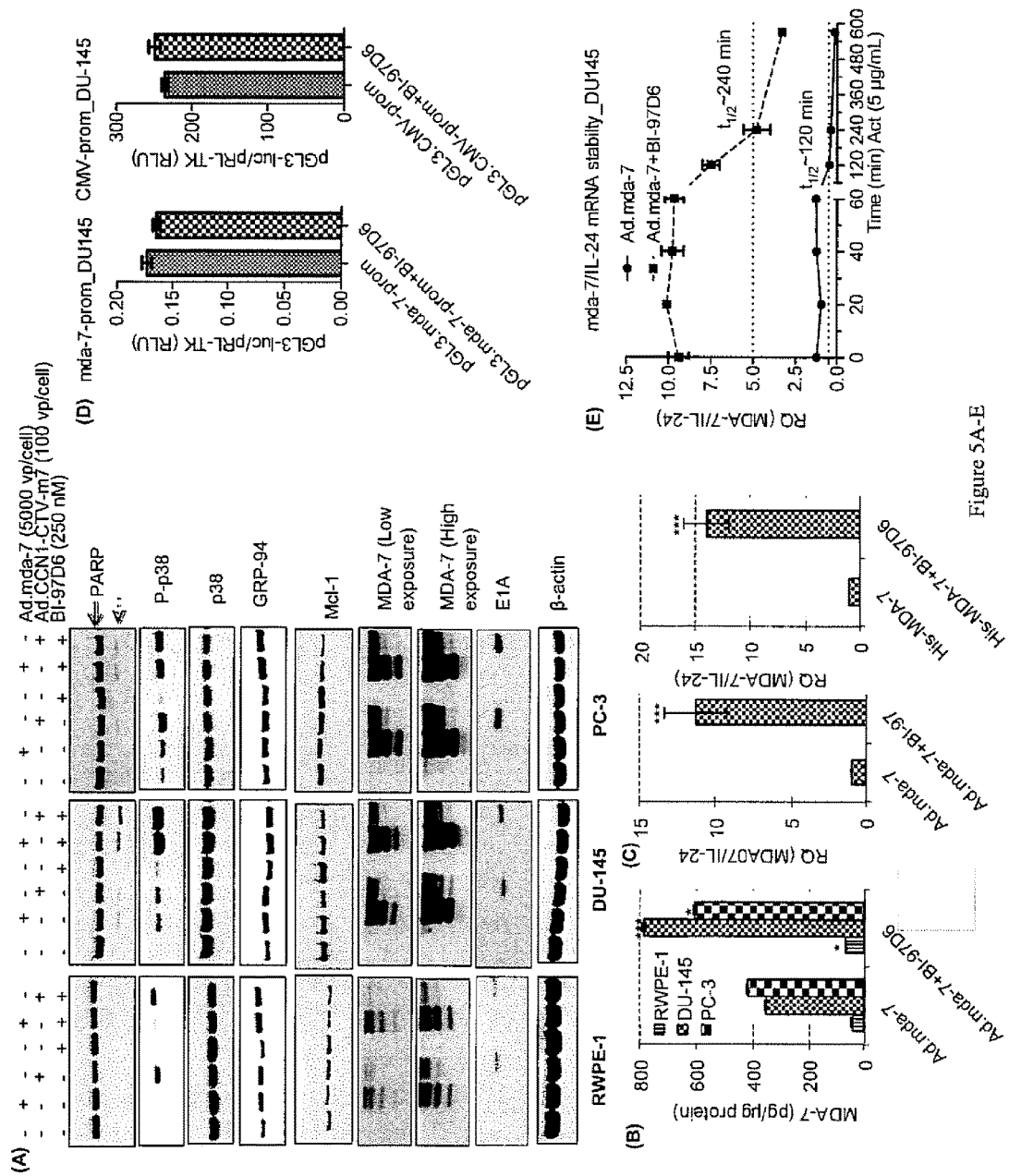
FIG. 5A-E. BI-97D6 potentiates mda-7/IL-24-induced apoptosis by enhancing ER stress-regulated proteins as well as by enhancing the translation of mda-7/IL-24 mRNA. A, DU-145, PC-3 and normal RWPE-1 cells were infected with 5000 vp/cell of Ad.mda-7 or 100 vp/cell of Ad.CCN1-E1A-mda-7 (Ad.CCN1-CTV-m7) followed by BI-97D6 (250 nM) treatment. Cell lysates were prepared 48-h post infection and Western blotting was performed. B, Quantification of MDA-7/IL-24 protein in the treated cells using human IL-24 Elisa Kit. C, q-PCR of DU-145 cells treated with Ad.mda-7 or recombinant His-MDA-7 protein with BI-97D6. GAPDH was taken as loading control for relative quantification of coda-7/IL-24 mRNA. D, RLU of mda-7-prom (pGL3.mda-7-prom-luc) and CMV-prom (pGL3.CMV-prom-luc) after normalization with pRL-TK. E, RNA stability of mda-7/IL-24 by BI-97D6.

BI-97D6 potentiates mda-7/IL-24-induced apoptosis by enhancing endoplasmic reticulum (ER) stress-regulated proteins as well as by enhancing the translation of mda-7/IL-24 mRNA. DU-145, PC-3 and normal RWPE-1 cells were infected with 5000 vp/cell of Ad.mda-7 or 100 vp/cell of Ad.CCN1-E1A-mda-7 (Ad.CCN1-CTV-m7) followed by BI-97D6 (250 nM) treatment. Cell lysates were prepared 48-h post infection and Western blotting (WB) and ELISA was performed. q-PCR of DU-145 cells treated with Ad.mda-7 or recombinant His-MDA-7 protein with BI-97D6 was done where GAPDH was used as the loading control for relative quantification of mda-7/IL-24 mRNA. RLU of mda-7-prom (pGL3.mda-7-prom-luc) and CMV-prom (pGL3.CMV-prom-luc) after normalization with pRL-TK was also conducted. Half-life of mRNA of mda-7/IL-24 was determined. The results are presented in FIG. 5.

Conclusions:
1. There was an increase in phosphorylation of p38 as well as the ER stress marker GRP-94 following Ad.mda-7 or Ad.CCN1-E1A-mda-7 (Ad.CCN1-CTV-m7) treatment, which was further, increased following combination treatment.
2. MDA-7/IL-24 expression was lower in Ad.CCN1-E1A-mda-7 (Ad.CCN1-CTV-m7) as compared to Ad.mda-7 infected cells, which was partly due to the lower M.O.I. (100 vp/cell) of Ad.CCN1-E1A-mda-7 (Ad.CCN1-CTV-m7) as compared to the higher MOI (5000 vp/cell) of Ad.mda-7.
3. However, both infective doses promoted similar levels of induction of ER stress proteins, i.e., p38 and GRP-94 which was further enhanced when combined with BI-97D6 leading to induction of apoptosis as evidenced by PARP cleavage.
4. Anti-apoptotic Mcl-1 expression is also found to decrease in combinatorial treatment.
5. PARP cleavage was not as prominent in PC-3 as compared to DU-145, partly due to intrinsic therapy and apoptotic resistance of PC-3 as compared to DU-145 using a similar MOI of Ads. Moreover, PC-3 with reduced expression of CAR led to minimal entry of Ad and transgene expression, but interestingly a combinatorial synergistic effect of Ad.CCN1-CTV-m7 and BI-97D6 was observed as compared to either agent alone.
6, The selective replication of Ad.CCN1-E1A-mda-7 (Ad.CCN1-CTV-m7) in PC cancers was evident from the detection of E1A expression in DU-145 and PC-3 infected cells as compared to normal immortal prostate epithelial cell line, RWPE-1.
7. Interestingly, it was observed that the BID mimetic BI-97D6 enhanced the expression of MDA-7/IL-24 protein as measured by quantitative ELISA.
8. It was found that BI-97D6 stabilizes mda-7/IL-24 at the mRNA level, which led to production of increased amounts of MDA-7/IL-24 protein, thereby inducing a synergistic effect.
9. Promotion of cancer-specific apoptosis by mda-7/IL-24 along with the cancer-specific oncolytic effects of Ad.CCN1-E1A-mda-7 (Ad.CCN1-CTV-m7) are more pronounced after longer exposure. The CTVs are expected to replicate exponentially with time producing elevated levels of secreted MDA-7/IL-24. In these contexts, a profound effect in vivo in reducing tumor size with minimal effects on normal cells is observed.

Figure 6:
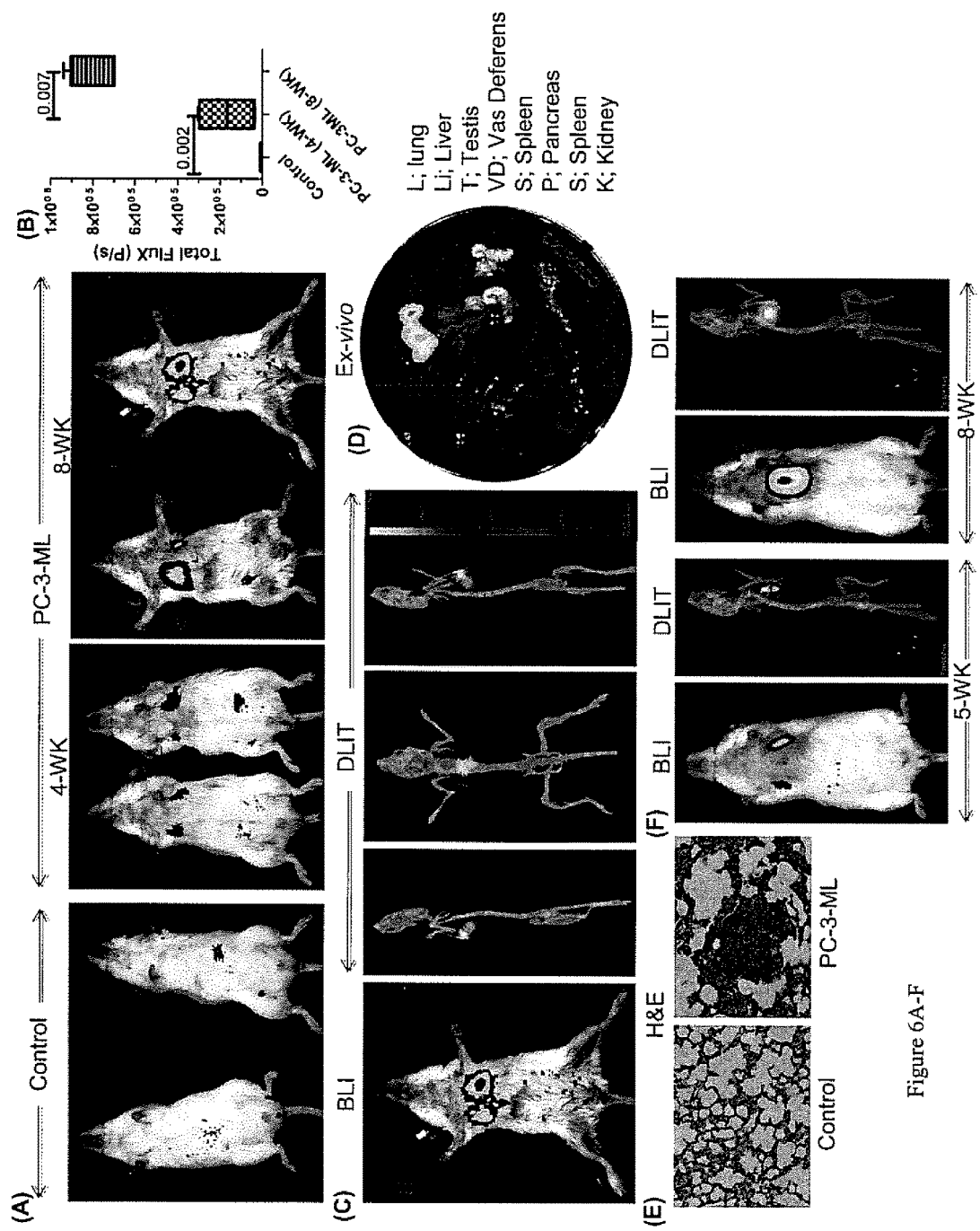
FIG. 6A-F. Utility of tCCN1-prom in the diagnosis of prostate cancer metastases. $3 \times 10^6$ PC-3ML cells were injected in 2-3 month old SCID mice to induce lung metastases. pGL3.CCN1-luc/PEI nanocomplexes were systemically injected via tail vein route, and BLI imaging was done 48-h post injection of plasmid/PEI nanocomplexes. A, BLI of SCID mice harboring lung metastases and matched age group mice (control). B, Quantification of BLI signal as metastasis progresses. C, BLI and 3D-BLI (Diffused light imaging tomography; DLIT) of SCID mice at 8-wk post injection of PC-3ML cells. D, The organs were dissected from the mice and ex-vivo imaging of organ was performed. E, H&E of control vs. PC-3ML cells harboring metastatic mice. F, DLIT of 5-wk and 8-wk post injected PC-3ML cells harboring SCID mice showing the intensity and location of the signal.

Example 6. Utility of tCCN1-Prom in the Diagnosis of Prostate Cancer Metastases $3 \times 10^6$ PC-3ML cells were injected in 2-3 month old SCID mice to induce lung metastases. pGL3.CCN1-luc/PEI nanocomplexes were systemically injected via the tail vein route, and BLI imaging was done 48-h post injection of plasmid/PEI nanocomplexes. The results are presented in FIG. 6, Conclusions:
1. tCCN1-Prom activity increases with cell aggressiveness, and tCCN1-prom is a valuable tool for imaging purposes and for studying the progress of metastases.
2. PC-3-ML cells (PC-3 cells obtained from metastatic lesions) were injected in 2-3 month old SCID male mice by the intracardiac route.
3. Mice were observed for any signs of metastases or weakness. Mice were imaged after 4-5 week post injection of cells after performing in vivo transfection using pGL3.CCN1-luc+/PEI nanocomplexes.
4. It was clearly shown that a signal is obtained especially from the lung region, which increases with increasing number of days post-injection of cells. There was a significant difference (p<0.002) in control vs. metastatic group and a significant difference (p<0.007) was also found between metastatic groups of 4-week post injection vs. 8-week post injection of PC-3ML cells.
5. To know the exact location and luminescence of the tumor, Diffused light imaging tomography (DLIT) was done. This technique gives the precise location and the strength of luminescence in tumors, which can then be further reconstructed with digital anatomical structures of the mice to determine the location of metastases.

6. By using 2D-BLI and 3D-DLIT, it was found that the BLI signal was evident from the lungs of the mice.
7. To further validate this approach, mice were dissected and the organs were removed and ex-vivo BLI of each organ was performed. It was found that the BLI signal was indeed observed from mouse lungs due to metastases, which was further verified by FLU staining of the lung sections, thus validating the approach of 2D-BLI in monitoring the location of the prostate cancer metastases.
8. To utilize the 2D-BLI and 3D-DLIT in monitoring tumor metastases, one representative mouse showing an intense BLI signal after 5-weeks was kept for further monitoring the growth of metastases in the lungs.
9. It was clearly evident that there was an increased signal of BLI from the lung of the mouse after 8-weeks, indicating the growth of metastatic PC-3-ML cells.
10. These results have clinical significance as far as detection of cancer metastases are concerned. These techniques can be integrated with already established imaging techniques and screening approaches to detect and monitor the progression and prognosis of prostate and other cancers displaying metastasis.

Figure 7:
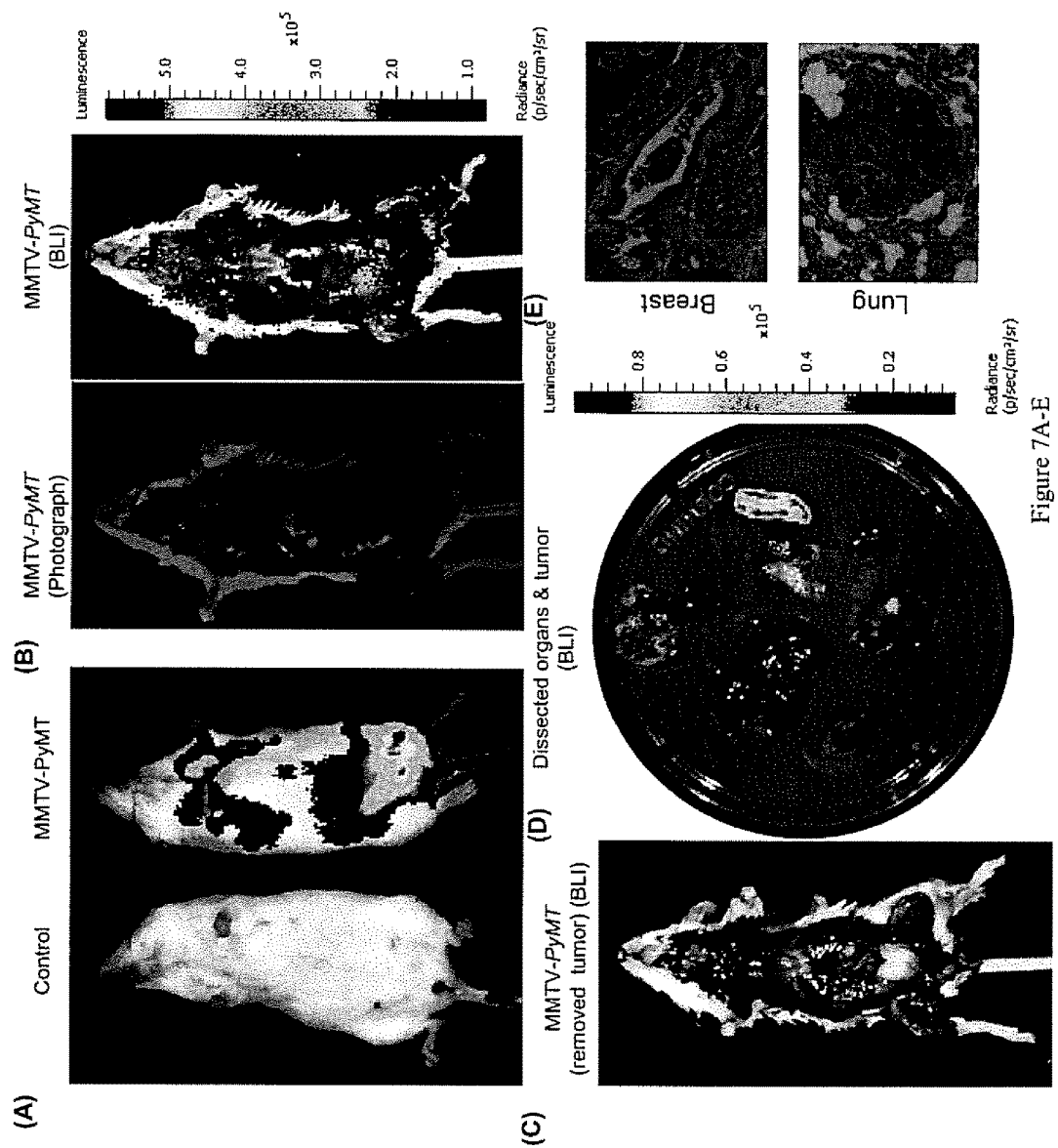
FIG. 7A-E. Bioluminescence imaging (BLI) of female MMTV-PyMT transgenic mice after transient transfection with pCCN1-luc/PEI. A, BLI image of control or FVB (MMTV-PyMT(−)) and MMTV-PyMT mice of same matched age group. B, to observe the luminescence signal obtained from BLI imaging, an incision cut was made through the skin to observe the gross anatomical view of organs and peritoneum. C and D, tumors were removed from mice and the mice were further imaged to see metastases from organs or other sites apart from the primary tumor. Dissected organs and tumor were imaged to observe the source of luminescence signal. E, H&E staining of lung and breast tissue to confirm the tumor formation and metastases.

Example 7. Bioluminescence Imaging (BLI) of Female MMTV-PyMT Transgenic Mice after Transient Transfection with pCCN1-luc/PEI pGL3.CCN1-luc/PEI nanocomplexes were injected in control or FVB (MMTV-PyMT (−) and MMTV-PyMT mice) via the intraductal route. D-luciferin (150 mg/kg body weight) was injected i.p. 48-h post injection of plasmid/PEI followed by image acquisition by Xenogen IVIS Spectrum (Caliper Life Sc., Perkin Elmer), and image processing was done using Living Image Module 4.3.1 (Perkin Elmer). The results are presented in FIG. 7.

Conclusions:
1. To check the cancer selective activity of tCCN1-Prom, we checked BLI imaging in female transgenic MMTV-PyMT mice after transient transfection of pCCN1-luc/PEI,
2. BLI approach utilizing the tCCN1-Prom-based luciferase activity detects the primary tumor as well as micrometastases at secondary sites (lung), and may also detect disseminated tumor cells (DTC).
3. Minimal or reduced background luminescence was detected in control or MMTV-PyMT(−) mice, further strengthening the utility of tCCN1-Prom in detecting invasive or metastatic tumors in female animals.

Example 8

Figure 8:
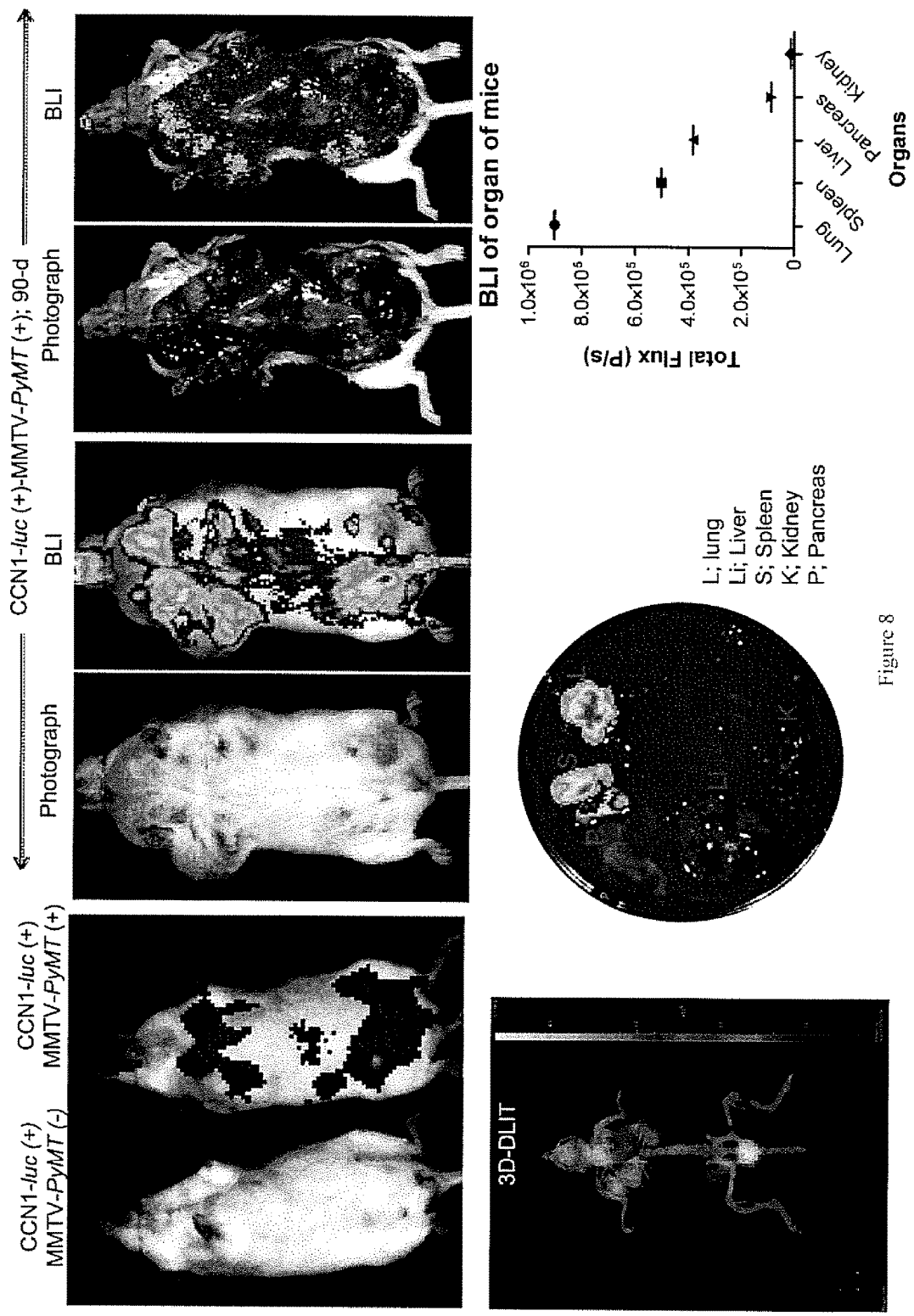
FIG. 8. Bioluminescence imaging (BLI) of CCN1-luc-MMTV-PyMT compound transgenic animals (CanView and MetaView Mice). D-luciferin (150 mg/kg body weight) was injected i.p. followed by image acquisition by Xenogen IVIS Spectrum (Caliper Life Sc., Perkin Elmer), and image processing was done using Living Image Module 4.3.1 (Perkin Elmer). To observe the luminescence signal obtained from BLI imaging, an incision cut was made through the skin to observe the gross anatomical view of organs and the peritoneum. Different organs were collected and ex-vivo imaging was performed to check for signs of metastases. 3D-DLIT was performed to know the location or depth and strength of the bioluminescence signal.

Bioluminescence imaging (BLI) of CCN1-luc-2-MMTV-PyMT compound transgenic animals (CanView or MetaView Mice). D-luciferin (150 mg/kg body weight) was injected i.p. followed by image acquisition by Xenogen IVIS Spectrum (Caliper Life Sc., Perkin Elmer), and image processing was done using Living Image Module 4.3.1 (Perkin Elmer). To observe the luminescence signal obtained from BLI imaging, an incision cut was made through the skin to observe the gross anatomical view of organs and the peritoneum. Different organs were collected and ex-vivo imaging was performed to check for signs of metastases. 3D-DLIT was performed to know the location or depth and strength of the bioluminescence signal. The results are presented in FIG. 8, Conclusions:
1. The success of transient expression of tCCN1-Prom driven luciferase expression in detecting primary invasive tumor and metastases prompted utilization of the BLI imaging approach in monitoring tumor progression and invasion in female transformed compound transgenic CCN1-luc-MMTV-PyMT (tCCN1-luc-MMTV-PyMT) animals (CanView and Meta View Mice).
2. These CanView or MetaView Mice were obtained by crossing transgenic CCN1-luc2 (tCCN1-luc2) female mice with MMTV-PyMT male mice. It was found that transformed CCN1-luc2 (tCCN1-luc2) mice, i.e., CCN1-luc-MMTV-PyMT (tCCN1-luc-MMTV-PyMT) animals (CanView or MetaView Mice), showed luminescence signals.
3. The BLI signal was only obtained from the tumor and partly from the metastatic cells harbored in different organs (e.g., lung, liver, spleen) as confirmed by in viva and ex vivo imaging.
4. 3D-BLI or 3D-DLIT was used to measure the depth and strength of the luminescence signal from the CanView or MetaView Mice.
5. The luminescence signal was specific as evident from observing the signal only from the tumor sites without any background signal from non-specific sites or organs, confirming the role of tCCN1-Prom upregulation and its potential in BLI-based non-invasive monitoring of tumor progression Example 9. Tumor Kinetics Study in CCN1-luc-MMTV-PyMT (tCCN1-luc-MMTV-PyMT) Mice Mice were imaged over various periods of time (40 days-90 days) to monitor tumor growth pattern and metastases. Image acquisition was done in DLIT mode using an IVIS spectrum and analyzed by Living Image 4.3.1. 2D-BLI and 3D Reconstructed DLIT image of the same mice were shown. The total flux of the mice over different time periods was measured and plotted using GraphPad Prism 5.0 and non-linear regression curve fit was done. Mice were periodically sacrificed and H&E staining was performed for further confirmation. $r^2=0.9675$ indicated a high correlation between total flux and the tumor size (increases with the number of days).

Figure 9:
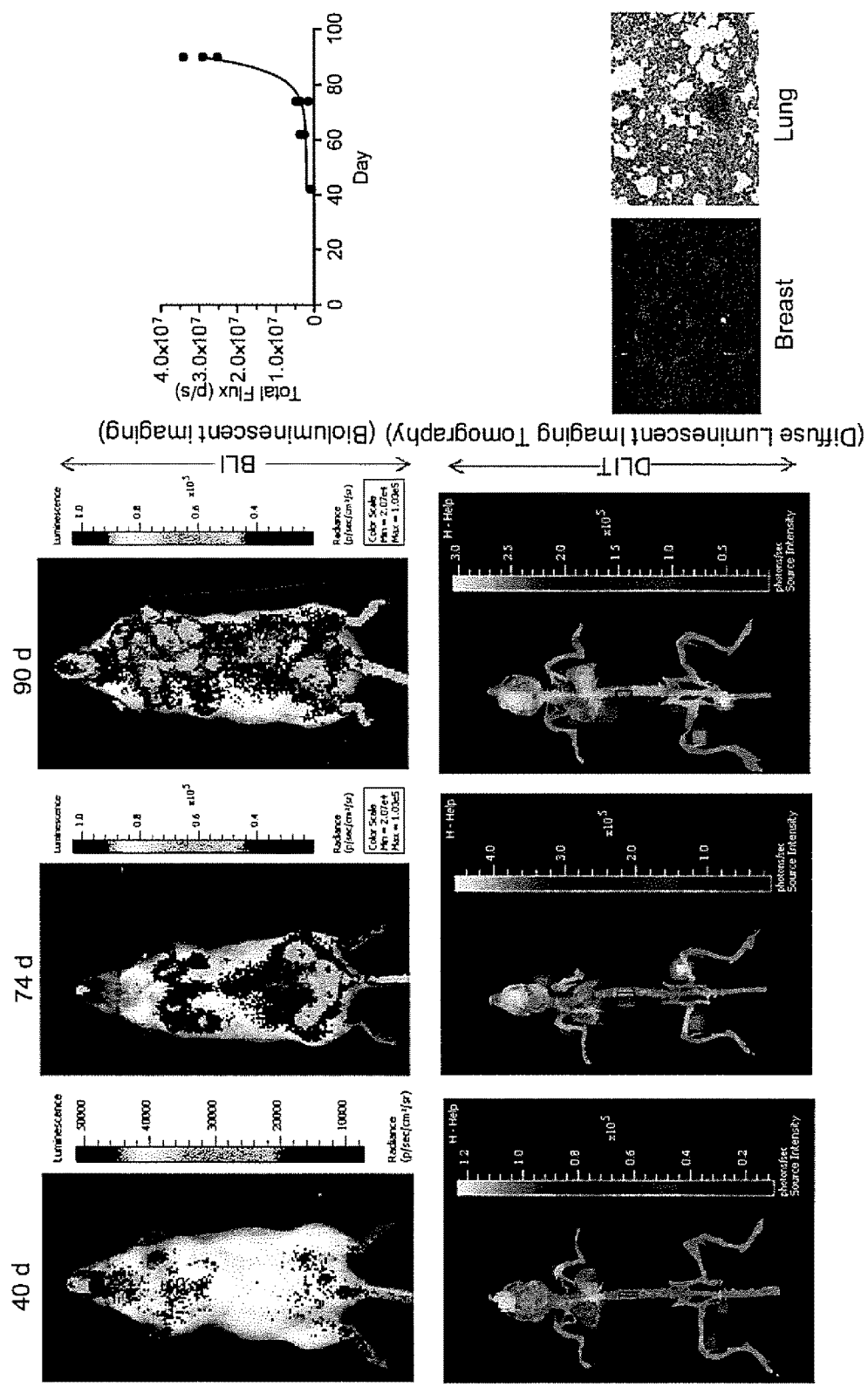
FIG. 9. Tumor kinetics study in CCN1-luc-MMTV-PyMT mice. Mice were imaged over various periods of time (40 day-90 day) to monitor tumor growth pattern and metastases. Image acquisition was done in DLIT mode using an IVIS spectrum and analyzed by Living Image 4.3.1. 2D-BLI and 3D Reconstructed DLIT image of the same mice were shown. The total flux of the mice over different time periods was measured and plotted using GraphPad Prism 5.0 and non-linear regression curve fit was done. $r^2$=0.9675 indicated a high correlation between total flux and the tumor size (increases with the number of days) indicating the specificity of tCCN1-prom based BLI in detection of tumor and invasion. The luminescence signal intensity increases with the size of tumor and lung metastases were also observed at the later stage of the tumor. Mice were periodically sacrificed and H&E staining was performed for further confirmation. Representative figure of H&E staining of 70-80 day old CCN1-luc-MMTV-PyMT mice.

The results are presented in FIG. 9. As can be seen, the luminescence signal intensity increased with the size of tumor and lung metastases were also observed at the later stages of the tumors, indicating the specificity of tCCN1-prom based BLI in detection of tumor location, size and extent of invasion, as well as metastasis.

Conclusions:
1. BLI approach with DLIT can be used to locate the tumor mass and metastases in live intact animals.
2. This imaging approach in CanView or MetView mice can be used to monitor the progression of the disease in individual subjects.
3. The detection of BLI signal is found to be a more sensitive way of detecting tumors than by simple palpable approach and caliper measurement.
4. This approach can be utilized in other cancers such as those in the pancreas where the organ is located internally.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

All patents and patent applications and publications cited herein are hereby incorporated by reference in entirety.

REFERENCES

1. Terada N, Shiraishi T, Zeng Y, Mooney S M, Yeater D B, Mangold L A, Partin A W, Kulkarni P, and Getzenberg R H, *Cyr61 is regulated by cAMP-dependent protein kinase with serum levels correlating with prostate cancer aggressiveness*. Prostate, 2012. 72(9): 966-76.
2. O'Brien T P, Yang G P, Sanders L, and Lau L F, *Expression of cyr61, a growth factor-inducible immediate-early gene*. Mol Cell Biol, 1990. 10(7): 3569-77.
3. Han J S, Macarak E, Rosenbloom J, Chung K C, and Chaqour B, *Regulation of Cyr61/CCN1 gene expression through RhoA GTPase and p38MAPK signaling pathways*. Eur J Biochem, 2003. 270(16): 3408-21.
4. Meyuhas R, Pikarsky F, Tavor E, Klar A, Abramovitch R, Hochman J, Lago T G, and Honigman A, *A Key role for cyclic AMP-responsive element binding protein in hypoxia-mediated activation of the angiogenesis factor CCN1 (CYR61) in Tumor cells*. Mol Cancer Res, 2008. 6(9): 1397-409.
5. Holloway S E, Beck A W, Girard L, Jaber M R, Barnett C C, Jr., Brekken R A, and Fleming J B, *Increased expression of Cyr61 (CCN1) identified in peritoneal metastases from human pancreatic cancer*. J Am Coll Surg, 2005. 200(3): 371-7.
6. O'Kelly J, Chung A, Lemp N, Chumakova K, Yin D, Wang H J, Said J, Gui D, Miller C W, Karlan B Y, and Koeffler H P, *Functional domains of CCN1 (Cyr6.1) regulate breast cancer progression*. Int J Oncol, 2008. 33(1): 59-67.
7. Dash R, Su Z Z, Lee S G, Azab B, Boukerche H, Sarkar D, and Fisher P B, *Inhibition of AP-1 by SARI negatively regulates transformation progression mediated by CCN1*. Oncogene, 2010. 29(31): 4412-23.
8. Lv H, Fan E, Sun S, Ma X, Zhang X, Han D M, and Cong Y S, *Cyr61 is up-regulated in prostate cancer and associated with the p53 gene status*. J Cell Biochem, 2009. 106(4): 738-44.
9. Sarkar S, Azab B, Quinn B A, Shen X, Dent P, Klibanov A L, Emdad L, Das S K, Sarkar D, and Fisher P B, *Chemoprevention gene therapy (CGT) of pancreatic cancer using perillyl alcohol and a novel chimeric serotype cancer terminator virus*. Curr Mol Med, 2014. 14(1): 125-40.
10. Dash R, Azab B, Quinn B A, Shen X, Wang X Y, Das S K, Rahmani M, Wei J, Hedvat M, Dent P, Dmitriev I P, Curiel D T, Grant S, Wu B, Stebbins J L, Pellecchia M, Reed J C, Sarkar D, Fisher P B. *Apogossypol derivative BI-97C1 (Sabutoclax) targeting Mcl-1 sensitizes prostate cancer cells to mda-7/IL-24-mediated toxicity*. Proc Natl Acad Sci USA. 2011 May 24; 108(20:8785-90.

We claim:

1. A recombinant vector comprising a truncated connective tissue growth factor/cysteine rich protein/nephroblastoma overexpressed gene-1 (CCN1) cancer selective promoter comprising the nucleotide sequence as set forth in SEQ ID NO: 1.

2. The recombinant vector of claim 1, wherein said truncated CCN1 cancer selective promoter is operably linked to at least one gene of interest.

3. The recombinant vector of claim 1, wherein said recombinant vector is a viral vector.

4. The recombinant vector of claim 3, wherein said viral vector is selected from the group consisting of: an adenoviral vector, a lentiviral vector, a herpes simplex virus vector, a measles virus vector, and a vaccinia virus vector.

5. The recombinant vector of claim 2, wherein said at least one gene of interest encodes one or more of an anticancer agent, an imaging agent, and a gene that is required for viral replication.

6. A mammalian cell comprising the recombinant vector according to claim 1.

7. The cell of claim 6, wherein said mammalian cell is a cancer cell.

8. A method of treating cancer in a patient in need thereof, comprising administering to said patient a composition comprising the recombinant vector of claim 5, wherein said at least one gene of interest comprises a gene encoding an anticancer agent, wherein said anticancer agent is expressed in the subject at a level effective to exert an anticancer effect, and wherein said cancer is bladder cancer, brain cancer, breast carcinoma, cervical carcinoma, colorectal cancer, endometrial carcinoma, esophageal carcinoma, gastric cancer, gestational trophoblastic disease, hematopoietic cell cancer, hepatocarcinoma, lung cancer, melanoma, neuroblastoma, osteosarcoma, ovarian carcinoma, pancreatic cancer, prostate cancer, renal cancer, retinoblastoma, uterine sarcoma, vaginal carcinoma, or vulvar carcinoma.

9. The method of claim 8, wherein the gene encoding the anticancer agent is a melanoma differentiation-associated 7/interleukin 24 (mda-7/IL-24) gene.

10. The method of claim 8, wherein the vector is a viral vector and comprises a gene required for viral replication operably linked to a cancer-specific or cancer-selective promoter.

11. A method of imaging cancer in a patient in need thereof, comprising administering to said patient a composition comprising the recombinant vector of claim 5, wherein said at least one gene of interest comprises a gene encoding an imaging agent, and detecting a signal from the imaging agent.

12. The method of claim 11, wherein the vector is a non-viral vector.

13. The method of claim 11, wherein the vector is a viral vector and further comprises a gene required for viral replication operably linked to a cancer-specific or cancer-selective promoter.

14. The recombinant vector of claim 5, wherein the vector is a viral vector, and wherein the vector, in addition to the truncated CCN1 cancer selective promoter comprising SEQ ID NO: 1, further comprises one or more cancer-specific or cancer-selective promoters operably linked to a gene encoding one or more of an anticancer agent, an imaging agent, and a gene required for viral replication.

15. The vector of claim 14, wherein the CCN1 cancer selective promoter is operably linked to gene encoding an anticancer agent.

16. The vector of claim 14, wherein the CCN1 cancer selective promoter is operably linked to a gene encoding an imaging agent.

17. The vector of claim 14, wherein the CCN1 cancer selective promoter is operably linked to a gene required for viral replication.

18. The vector of claim 14, wherein at least one of the one or more cancer-specific or cancer-selective promoters is a progression elevated gene-1 promoter (PEG-Prom).

19. A nanoparticle comprising the vector of claim 5.

* * * * *

```
                          SEQUENCE LISTING

<160> NUMBER OF SEQ ID NOS: 5

<210> SEQ ID NO 1
<211> LENGTH: 838
<212> TYPE: DNA
<213> ORGANISM: Artificial Sequence
<220> FEATURE:
<223> OTHER INFORMATION: Synthetic promoter

<400> SEQUENCE: 1
tccaaaaaca aacaagtaca acatacccaa aagagggaag ggctggagga gtgggggaga      60
cctctgcctg ggaatttgcc agacgatggg caagtttccc cccgccccac ccccccccc     120 gccttttcat tcataaatgc cactgtgggt attaatttgc aattcactga actttgctaa    180
taaacatcat gccaaagctt tgggacttgt tccgaacacg cctctttgaa gtccacaaat    240
attcctgact cagagacaca ctcctcttcc ccgttctact ctttcaacag ataacttgcc    300
tctcaccttc gctgtaaaaa agcaaacagc tcactgcctt cccgggtgag ggcttcagtg    360
gctgcccggt caactcgcat caccaaacaa aacgactttt gttcctccct ctcaggtcct    420
cccacccacc cagtccaggc aaagttctga actggccccc tcgcccctca cgaccctcca    480
actaccatca ccaccatcac gccccaaaga acccttccca acataagtcg taatttaagg    540
tggaaaaaac gaactgtttt cttgacgggt ctgggacaca cacacacaca cacacacaca    600
cacacaccga actgtttct tgacgggtct gggagacaca cacacacaca cacacaca     660 cacacacaca cacacacaca caaaggtgca atggggccag gggaggcgct tggcagcagc    720
ccgcgccaac cagcattcct gagatgtttg agaattctgg aacgcgcaga cagagccgac    780
gtcactgcaa cacgcggcgc ctccgccggc ccgtataaaa ggcgggctcc ggggcgcc      838

<210> SEQ ID NO 2
<211> LENGTH: 24
```

```
<212> TYPE: DNA
<213> ORGANISM: Artificial Sequence
<220> FEATURE:
<223> OTHER INFORMATION: Synthetic oligonucleotide primer

<400> SEQUENCE: 2
tccaaaaaca aacaagtaca acat                                          24

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 3
ggcgccccgg agcccgcctt ttata                                         25

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 4
ccctctgcta accatgttca tgc                                           23

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 5
tcttgctcac gaatacgacg gtg                                           23
```